US010253121B2

(12) United States Patent
Boller et al.

(10) Patent No.: US 10,253,121 B2
(45) Date of Patent: Apr. 9, 2019

(54) METHOD OF PRODUCING POLYETHYLENE AND POLYETHYLENE THEREOF

(71) Applicant: UNIVATION TECHNOLOGIES, LLC, Houston, TX (US)

(72) Inventors: Timothy M. Boller, Houston, TX (US); Ching-Tai Lue, Sugar Land, TX (US); Francis C. Rix, League City, TX (US); Daniel P. Zilker, Jr., Charleston, WV (US); C. Jeff Harlan, Houston, TX (US); James M. Farley, League City, TX (US); Fathi D. Hussein, Hilton Head Island, SC (US); Dongming Li, Houston, TX (US); Steven A. Best, The Woodlands, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/117,343

(22) PCT Filed: Feb. 10, 2015

(86) PCT No.: PCT/US2015/015132
§ 371 (c)(1),
(2) Date: Aug. 8, 2016

(87) PCT Pub. No.: WO2015/123172
PCT Pub. Date: Aug. 20, 2015

(65) Prior Publication Data
US 2016/0347874 A1 Dec. 1, 2016

Related U.S. Application Data

(60) Provisional application No. 61/938,472, filed on Feb. 11, 2014, provisional application No. 61/938,466, (Continued)

(51) Int. Cl.
*C08F 4/653* (2006.01)
*C08F 4/6592* (2006.01)
(Continued)

(52) U.S. Cl.
CPC ............ *C08F 210/16* (2013.01); *C07F 17/00* (2013.01); *C08F 2/00* (2013.01); *C08F 2/34* (2013.01);
(Continued)

(58) Field of Classification Search
CPC .............. C08F 4/65904; C08F 4/65912; C08F 4/65925; C08F 210/16; C08L 23/08; C08L 23/0815
See application file for complete search history.

(56) References Cited

U.S. PATENT DOCUMENTS 6,372,868 B1    4/2002    Szul et al.
6,610,799 B1    8/2003    Follestad et al.
(Continued)

FOREIGN PATENT DOCUMENTS

JP    2003105029    4/2003
JP    2009126902    6/2009
(Continued)

OTHER PUBLICATIONS

International Search Report & Written Opinion for related PCT Application PCT/US2015/015132, dated Jul. 30, 2015 (17 pgs).

*Primary Examiner* — Caixia Lu
(74) *Attorney, Agent, or Firm* — Brooks, Cameron & Huebsch, PLLC

(57) ABSTRACT

A system and method of producing polyethylene, including: polymerizing ethylene in presence of a catalyst system in a reactor to form polyethylene, wherein the catalyst system includes a first catalyst and a second catalyst; and adjusting reactor conditions and an amount of the second catalyst fed
(Continued)

to the reactor to control melt index (MI), density, and melt flow ratio (MFR) of the polyethylene.

10 Claims, 8 Drawing Sheets

Related U.S. Application Data filed on Feb. 11, 2014, provisional application No. 61/981,291, filed on Apr. 18, 2014, provisional application No. 61/985,151, filed on Apr. 28, 2014, provisional application No. 62/032,383, filed on Aug. 1, 2014, provisional application No. 62/088,196, filed on Dec. 5, 2014, provisional application No. 62/087,914, filed on Dec. 5, 2014, provisional application No. 62/087,911, filed on Dec. 5, 2014, provisional application No. 62/087,905, filed on Dec. 5, 2014.

(51) Int. Cl.

| | | |
|---|---|---|
| *C08F 210/16* | (2006.01) | |
| *C08L 23/08* | (2006.01) | |
| *C08F 4/659* | (2006.01) | |
| *C07F 17/00* | (2006.01) | |
| *C08F 210/02* | (2006.01) | |
| *C08F 4/76* | (2006.01) | |
| *C08F 2/00* | (2006.01) | |
| *C08F 2/34* | (2006.01) | |
| *C08J 5/18* | (2006.01) | |
| *C08F 210/14* | (2006.01) | |
| *C08F 210/08* | (2006.01) | |

(52) U.S. Cl.
CPC ............ *C08F 4/65904* (2013.01); *C08F 4/76* (2013.01); *C08F 210/02* (2013.01); *C08J 5/18* (2013.01); *C08F 4/65912* (2013.01); *C08F 4/65916* (2013.01); *C08F 4/65925* (2013.01); *C08F 4/65927* (2013.01); *C08F 210/08* (2013.01); *C08F 210/14* (2013.01); *C08F 2410/02* (2013.01); *C08F 2420/00* (2013.01); *C08F 2420/01* (2013.01); *C08F 2500/01* (2013.01); *C08F 2500/02* (2013.01); *C08F 2500/08* (2013.01); *C08F 2500/09* (2013.01); *C08F 2500/10* (2013.01); *C08F 2500/11* (2013.01); *C08F 2500/12* (2013.01); *C08F 2500/13* (2013.01); *C08F 2500/18* (2013.01); *C08F 2800/20* (2013.01); *C08J 2323/08* (2013.01); *C08L 23/0815* (2013.01)

(56) References Cited

U.S. PATENT DOCUMENTS

| | | |
|---|---|---|
| 6,855,839 B2 | 2/2005 | McConville et al. |
| 6,943,227 B2 | 9/2005 | Ishihama et al. |
| 7,763,561 B2 | 7/2010 | McDaniel et al. |
| 8,067,518 B2 | 11/2011 | Davey et al. |
| 8,288,487 B2 | 10/2012 | Yang et al. |
| 8,664,140 B2 | 3/2014 | Schmitz et al. |
| 8,859,451 B2 | 10/2014 | Mihan et al. |
| 8,932,975 B2 | 1/2015 | Yang et al. |
| 8,999,875 B2 | 4/2015 | Fantinel et al. |
| 9,181,370 B2 * | 11/2015 | Sukhadia .............. C08F 210/02 |
| 9,346,896 B2 | 5/2016 | McDaniel et al. |
| 2002/0103310 A1 * | 8/2002 | Szul ........................ C08F 10/02 526/114 |
| 2002/0161141 A1 | 10/2002 | Mawson et al. |
| 2003/0008980 A1 | 1/2003 | Mawson et al. |
| 2003/0008988 A1 * | 1/2003 | Tincul .................. C08F 210/02 526/170 |
| 2004/0254308 A1 | 12/2004 | Schurzky et al. |
| 2007/0043176 A1 * | 2/2007 | Martin .................... C08F 10/00 526/64 |
| 2009/0240010 A1 | 9/2009 | McDaniel et al. |
| 2010/0076167 A1 | 3/2010 | McDaniel et al. |
| 2010/0249355 A1 | 9/2010 | Davis et al. |
| 2010/0292418 A1 | 11/2010 | Jorgensen et al. |
| 2010/0317904 A1 | 12/2010 | Small et al. |
| 2012/0010375 A1 | 1/2012 | Yang et al. |
| 2012/0046428 A1 * | 2/2012 | Kao ........................ C08F 10/00 526/113 |
| 2012/0059134 A1 | 3/2012 | Yang et al. |

FOREIGN PATENT DOCUMENTS

| | | |
|---|---|---|
| WO | 99/03897 | 1/1999 |
| WO | 0109200 | 2/2001 |
| WO | 0130861 | 5/2001 |
| WO | 2005044863 | 5/2005 |

* cited by examiner

100

METHOD OF PRODUCING POLYETHYLENE AND POLYETHYLENE THEREOF

RELATED APPLICATIONS

This application is a National Stage Application under 35 U.S.C. § 371 of International Application Number PCT/US2015/015132, filed Feb. 10, 2015 and published as WO 2015/123172 on Aug. 20, 2015, which claims the benefit to the following U.S. Provisional Applications 61/938,472, filed Feb. 11, 2014; 61/938,466, filed Feb. 11, 2014; 61/981,291, filed Apr. 18, 2014; 61/985,151, filed Apr. 28, 2014; 62/032,383, filed Aug. 1, 2014; 62/088,196, filed Dec. 5, 2014; 62/087,914, filed Dec. 5, 2014; 62/087,911, filed Dec. 5, 2014; 62/087,905, filed Dec. 5, 2014; the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution (MWD) as the reaction temperature is increased, for example, to increase production rates. Further, a single site catalyst will often incorporate comonomer among the molecules of the polyethylene copolymer at a relatively uniform rate.

The composition distribution (CD) of an ethylene alpha-olefin copolymer refers to the distribution of comonomer, which form short chain branches, among the molecules that compose the polyethylene polymer. When the amount of short chain branches varies among the polyethylene molecules, the resin is said to have a "broad" composition distribution. When the amount of comonomer per 1000 carbons is similar among the polyethylene molecules of different chain lengths, the composition distribution is said to be "narrow." It is generally known in the art that a polyolefin's MWD and CD will affect the different product attributes.

To reduce or to avoid certain trade-off among desirable attributes, bimodal polymers have become increasingly important in the polyolefins industry, with a variety of manufacturers offering products of this type. Whereas older technology relied on two-reactor systems to generate such material, advances in catalyst design and supporting technology have allowed for the development of single-reactor bimetallic catalyst systems capable of producing bimodal polyethylene. These systems are attractive both from a cost perspective and ease of use.

SUMMARY

Certain aspects relate to a system and method of producing polyethylene, including polymerizing ethylene in the presence of a catalyst system in a reactor to form polyethylene, wherein the catalyst system includes a first catalyst and a second catalyst. The techniques include adjusting reactor conditions and an amount of the second catalyst fed to the reactor to control melt index (MI), density, and melt flow ratio (MFR) of the polyethylene.

BRIEF DESCRIPTION OF THE DRAWINGS

FIG. 5A is a diagrammatical representation of techniques for generating targets or recipes, and producing, some of the exemplary BOCD polymers of Table 1, those listed in Table 2a.

DETAILED DESCRIPTION

Figure 1:
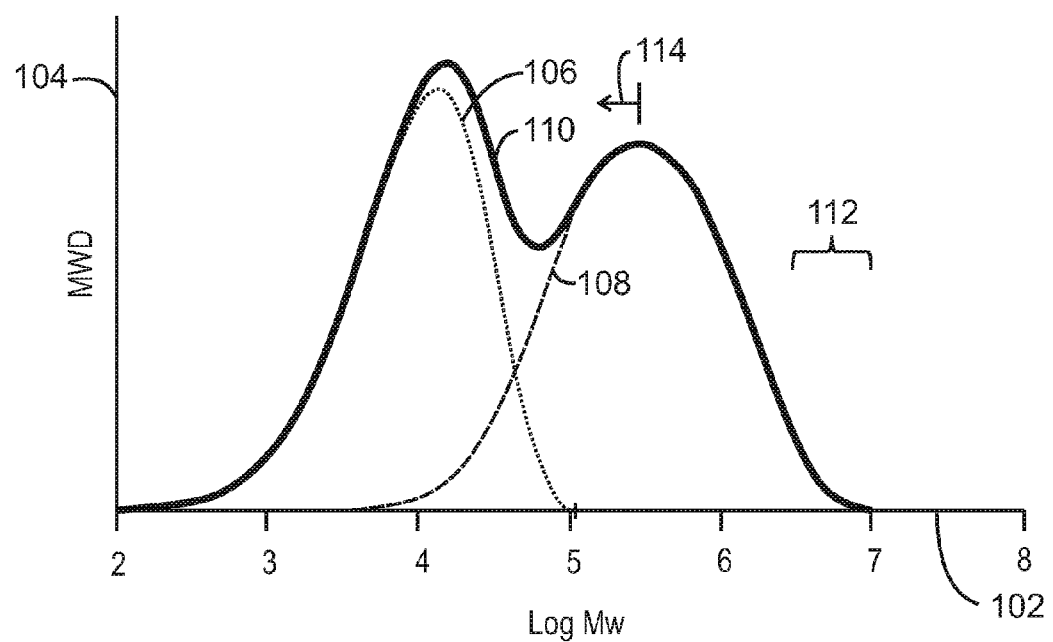
FIG. 1 is a representative plot of molecular weight distribution of polyolefin polymerized with a two catalyst system in accordance with embodiments described herein.

As discussed below for producing polyethylene, the catalyst trim ratio, the polymerization reactor temperature, and the polymerization reactor hydrogen and comonomer concentrations, may be varied to give a range of MFR at a substantially constant polyethylene density and MI (I-2). The techniques may beneficially accommodate a broad range of MI's with a given catalyst system. Moreover, in embodiments, MI control may be substantially decoupled from MFR control. For a catalyst system fed to the polymerization reactor, the polymer MI, MFR, density, and CD may be controlled by varying reactor conditions such as temperature, hydrogen concentration, and comonomer (e.g., 1-hexene, butene, etc.) concentration.

Embodiments of the present techniques are directed to catalyst systems and control of the polymerization reactor conditions to polymerize ethylene and any comonomer to form polyethylene. With respect to the polyethylene produced in the polymerization reactor, certain embodiments accommodate independent control of melt flow ratio (MFR) and composition from melt index (MI) and density, or vice versa. Indeed, embodiments may address MI and density from melt flow ratio (MFR) and the relationship between (i.e., combination of) MWD and CD composition. The techniques address inter-relationships among catalyst, polyolefin product, and polyolefin product performance. As appreciated by the skilled artisan for nomenclature, the MI without notation is I-2, and the MFR is the ratio of MI(I-21)/MI(I-2).

The properties and performance of the polyethylene may be advanced by the combination of: (1) selecting and feeding a dual catalyst system having a first catalyst trimmed with a second catalyst; and (2) varying reactor conditions such as reactor temperature, comonomer concentration, hydrogen concentration, and so on. With regard to some embodiments of the catalyst system, the first catalyst is a high molecular weight component and the second (trim) catalyst is a low molecular weight component. In other words, the first catalyst may provide primarily for a high molecular-weight portion of the polyethylene, and the second catalyst may provide primarily for a low molecular-weight portion of the polyethylene.

Thus, in some embodiments, a first catalyst such as metallocene HfP or bis(n-propylcyclopentadienyl) Hafnium dimethyl, shown as structure (I) below may be selected to produce a higher molecular weight component of the polymer. In examples, the first catalyst may be fed in a slurry to the polymerization reactor. A second catalyst such as the metallocene EthInd, or meso and rac entantiomers of di(1-ethylindenyl) zirconium dimethyl, shown as structures (II-A) and (II-B) below, may be selected to produce a low molecular weight component of the polymer. Some or all of the second catalyst may be fed as a trim catalyst into the catalyst slurry having the first catalyst in route to the polymerization reactor.

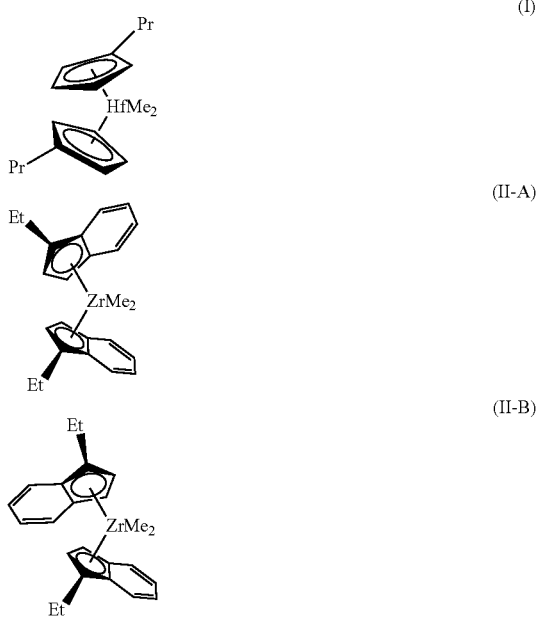

Of course, other metallocene catalysts (or non-metallocene catalysts), as described herein, may be selected, and other catalyst system configurations implemented. The particular metallocene catalysts selected may depend on the specified properties of the polymer and the desired downstream applications of the formed polymer resins, such for film, rotation molding, injection molding, blow-molding applications, pipe applications, and so on. The catalysts selected may include catalysts that facilitate good (high) or poor (low) incorporation of comonomer (e.g., 1-hexene) into the polyethylene, have a relatively high response to hydrogen concentration in the reactor or a relatively low response to reactor hydrogen concentration, and so on.

By using structures such as EthInd as the second catalyst trimmed on-line at various ratios onto slurry feeding the first catalyst such as the first metallocene catalyst HfP, along with varying reactor conditions including temperature, reaction-mixture component concentrations, and the like, beneficial polyethylene products may be formed. In an alternate example, a reverse trim is employed in that the LMW catalyst species EthInd is the first catalyst and the HMW catalyst species HfP is the second catalyst or catalyst trim. It should also be noted that for the various catalysts selected, some of the second catalyst may be initially co-deposited with the first catalyst on a common support, and the remaining amount of the second catalyst added as trim. Of course, again, other configurations of the catalyst system are contemplated.

In certain embodiments as indicated, the amount of second catalyst fed (or the catalyst trim ratio), and the reactor conditions (e.g., temperature and hydrogen concentration), may be varied to give a range of MFR while maintaining polyethylene density and MI (I-2). The embodiments may advantageously accommodate a broad range of MI's with the same catalyst system, e.g., the same dual catalyst system. Indeed, MI control may be substantially decoupled from MFR control. For a catalyst system fed to the polymerization reactor, the polymer MI, MFR, density and CD may be controlled by varying reactor conditions such as the reactor mixture including operating temperature, hydrogen concentration, and comonomer concentration in reaction mixture.

In the exemplary Table 1a below, example aspects of reactor control with respect to polyethylene properties are indicated. For instance, the hydrogen/ethylene (H2/C2) weight ratio or mol ratio may be an adjustment or control knob or a "primary" adjustment knob, for polyethylene MI adjustment. The comonomer/ethylene (C6/C2) weight ratio or mol ratio may be an adjustment or control knob or a "primary" adjustment knob, for polyethylene density. The reactor temperature and the weight or mol ratio of the two catalysts (or the catalyst trim ratio) may be an adjustment or control knobs for the polyethylene MFR. Other adjustment and control points are considered. Moreover, a primary property may be specified and controlled first. For example, the MFR may be selected as a primary property of the polymer, and a range of MFR values of the polymer consider for a given catalyst system used to produce the polymer. In that example approach with a range of MFR values as primary, other polymer properties such as MI and density may be fine-tuned. Further, the techniques for reactor control described herein including the factors considered in Table 1a may apply to (1) direct control of the reactor during the actual production of the polyethylene, (2) development of recipe targets for reactor conditions for various catalyst systems (and amounts) and polyethylene grades or products, (3) polyethylene product development, and so forth TABLE 1a

| | Reactor Control | | | |
| --- | --- | --- | --- | --- |
| | Temperature | C6/C2 | H2/C2 | Catalyst ratio |
| MI | | | X | |
| Density | | X | | |
| MFR | X | | | X |

Exemplary ranges of MFR include 20 to 40, 20 to 45, 20 to 50, 20 to 60, and so forth. Exemplary ranges of MI (grams/10 minutes) include 0.1 to 4 (e.g., for film), 5 to 50 or 100 (e.g., for molding such as rotational and/or injection molding), and so on. Exemplary ranges for density include 0.915 to 0.935, 0.912 to 0.940, 0.910 to 0.945, and the like.

It should be noted that without intelligently tailoring for specific MWD and CD, polyethylene copolymers usually exhibit trade-off paradigms among the desirable attribute, e.g., improving stiffness at the expense of toughness or improving processability at the expense of toughness. Control of these properties may be obtained for the most part by the choice of the catalyst system. Thus, the catalyst design is important for producing polymers that are attractive from a commercial standpoint. Because of the improved physical properties of polymers with the specially tailored MWD and CD beneficial for commercially desirable products, embodiments herein address the need for controlled techniques for forming polyethylene copolymers having a specific MWD and CD.

In examples, sets of reactor conditions for making narrow MFR (low 20s) and broad MFR (high 20s) products with a single catalyst such as 100% HfP may be identified and implemented. For instance, reactor temperature may be used as a primary control variable for MFR adjustment with the 100% HfP. Subsequently, at the chosen reactor temperature for a starting MFR, a trim-catalyst level may be added to further increase MFR until a pre-set MFR range is reached. The component concentrations in the polymerization mixture, such as hydrogen and comonomer (e.g., 1-hexene) concentrations, may be adjusted for specific MI and density targets of the polyethylene at the given MFR range. The amount of trim catalyst and reactor concentration adjustments may be repeated for various levels of MFR range and specific MI and density targets. In a particular example, a polyethylene polymer having a MI of about 1.0 dg/min and a density of about 0.918 g/cm3 may be produced as a tie point for each MFR level. Such may be beneficial in identifying catalyst-product-performance inter-relationships. Moreover, at each MFR level, additional grades for particular market interests may be noted.

Embodiments demonstrate a novel technology to independently control a polyethylene product's MFR and/or MWD and CD composition from its MI and density in a single reactor environment. Consequently, some polyethylene products may have a wide range of MWD and CD compositions and product attribute combinations. In examples, some of the polyethylene polymers may have the same or similar nominal MI and density but different MFR and MWD and CD. Other polyethylene polymers in the examples have the same or similar nominal MI (I-2), density, and MFR but are different in MWD and CD. In some of the examples, the MI may range from 0.1 to 5.0<1g/min, 0.5 to 1.0 dg/min, and other ranges, and the density may range from 0.912 to 0.940 g/cm3, 0.916 to 0.926 g/cm3, and other ranges.

While the discussion herein may focus on multiple catalysts on a catalyst support and introduced to a polymerization reactor, the present catalysts may be applied in a variety of configurations. For example, the catalysts may be applied separately in a single-reactor or multiple-reactor polymerization systems. The multiple catalysts may be applied on a common support to a given reactor, applied via different supports, and/or utilized in reactor systems having a single polymerization reactor or more than one polymerization reactor, and so forth. The discussion now turns to embodiments related to multiple catalysts, e.g., a first catalyst and a second catalyst, impregnated on a catalyst support for polymerization of monomer into a polymer.

A catalyst support impregnated with multiple catalysts may be used to form polymeric materials with improved balance of properties, such as stiffness, toughness, processibility, and environmental stress crack resistance. Such a balance of properties can be achieved, for example, by controlling the amounts and types of catalysts present on the support. Selection of the catalysts and ratios may adjust the combined molecular weight distribution (MWD) of the polymer produced. The MWD can be controlled by combining catalysts giving the desired weight average molecular weight (Mw) and individual molecular weight distributions of the produced polymer. For example, the typical MWD for linear metallocene polymers is 2.5 to 3.5. Blend studies indicate it would be desirable to broaden this distribution by employing mixtures of catalysts that each provides different average molecular weights. The ratio of the Mw for a low molecular weight component and a high molecular weight component would be between 1:1 and 1:10, or about 1:2 and 1:5. Again, when a support is impregnated with multiple catalysts, new polymeric materials with improved balance of stiffness, toughness and processability can be achieved, e.g., by controlling the amounts and types of catalysts present on the support. Appropriate selection of the catalysts and ratios may be used to adjust the MWD, short chain branch distribution (SCBD), and long-chain branch distribution (LCBD) of the polymer, for example, to provide a polymer with a broad orthogonal composition distribution (BOCD). The MWD, SCBD, and LCBDs would be controlled by combining catalysts with the appropriate weight average molecular weight (Mw), comonomer incorporation, and long chain branching (LCB) formation under the conditions of the polymerization. Polymers having a broad orthogonal composition distribution (BOCD) in which the comonomer is incorporated preferentially in the high molecular weight chains can lead to improved physical properties, for example, stiffness, toughness, processability, and environmental stress crack resistance (ESCR), among others. Because of the improved physical properties of polymers with orthogonal composition distributions needed for commercially desirable products, controlled techniques for forming polyethylene copolymers having a broad orthogonal composition distribution may be beneficial.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution as the reaction temperature is increased, for example, to increase production rates. Further, a single site catalyst will often incorporate comonomer among the molecules of the polyethylene copolymer at a relatively uniform rate. The molecular weight distribution (MWD) and the amount of comonomer incorporation can be used to determine a SCBD. For an ethylene alpha-olefin copolymer, short chain branching (SCB) on a polymer chain is typically created through comonomer incorporation during polymerization. Short chain branch distribution (SCBD) refers to the distribution of short chain branches within a molecule or among different molecules that comprise the polyethylene polymer. When the amount of SCB varies among the polyethylene molecules, the resin is said to have a "broad" SCBD. When the amount of SCB is similar among the polyethylene molecules of different chain lengths, the SCBD is said to be "narrow". SCBD is known to influence the properties of copolymers, for example, stiffness, toughness, extractable content, environmental stress crack resistance, and heat sealing, among other properties. SCBD of a polyolefin may be readily measured by methods known in the art, for example, Temperature Raising Elution Fractionation (TREF) or Crystallization Analysis Fractionation (CRYSTAF). A polyolefin's MWD and SCBD is largely dictated by the type of catalyst used and is often invariable for a given catalyst system. Ziegler-Natta catalysts and chromium based catalysts produce polymers with broad SCBD, whereas metallocene catalysts normally produce polymers with narrow SCBD. It has been long observed in the industry that there are trade-off paradigms among the different product attributes; most noticeably among stiffness, toughness, and processability (S/T/P). Since the introduction of metallocene in 1990s, some of such paradigms have been relaxed significantly with careful manipulations of molecular structure and composition in the product.

Employing multiple pre-catalysts that are co-supported on a single support mixed with an activator, such as a silica methylaluminoxane (SMAO), can provide a cost advantage by making the product in one reactor instead of multiple reactors. Further, using a single support also facilitates intimate mixing of the polymers and offers improved operability relative to preparing a mixture of polymers of different Mw and density independently from multiple catalysts in a single reactor. As used herein, a pre-catalyst is a catalyst compound prior to exposure to activator. The catalysts can be co-supported during a single operation, or may be used in a trim operation, in which one or more additional catalysts are added to catalysts that are supported.

The density of a polyethylene copolymer provides an indication of the incorporation of comonomer into a polymer, with lower densities indicating higher incorporation. The difference in the densities of the low molecular weight (LMW) component and the high molecular weight (HMW) component would preferably be greater than about 0.02, or greater than about 0.04, with the HMW component having a lower density than the LMW component. These factors can be adjusted by controlling the MWD and SCBD, which, in turn, can be adjusted by changing the relative amount of the two pre-catalysts on the support. This may be adjusted during the formation of the pre-catalysts, for example, by supporting two catalysts on a single support. In some embodiments, the relative amounts of the pre-catalysts can be adjusted by adding one of the components to a catalyst mixture en-route to the reactor in a process termed "trim." Feedback of polymer property data can be used to control the amount of catalyst addition. Metallocenes (MCNs) are known to trim well with other catalysts.

Further, a variety of polymers with different MWD, SCBD, and LCBD may be prepared from a limited number of catalysts. To do so, the pre-catalysts should trim well onto activator supports. Two parameters that benefit this are solubility in alkane solvents and rapid supportation on the catalyst slurry en-route to the reactor. This favors the use of MCNs to achieve controlled MWD, SCBD, and LCBD. Techniques for selecting catalysts that can be used to generate targeted molecular weight compositions, including BOCD polymer systems, may be employed.

FIG. 1 is a plot 100 of molecular weight distributions for a two catalyst system that includes a first catalyst that is a metallocene catalyst or a non-metallocene catalyst, and a second catalyst that is another metallocene, in accordance with embodiments described herein. In the plot 100, the x-axis 102 represents the log of the molecular weight, and the y-axis 104 represents the molecular weight distribution, i.e., the amount of each molecular weight that is present. Each of the catalysts can be selected to contribute a certain molecular weight component. For example, a metallocene catalyst, such as structure (II-A) or structure (II-B) may be selected to produce a low molecular weight component 106. Another metallocene, such as the catalyst shown in structure (I), or a non-metallocene, may be selected to produce a higher molecular weight component 108. The individual molecular weight components form a single molecular weight distribution (MWD) 110 for the polymer. Other metallocene catalysts, as described herein, may be selected. The particular metallocene catalysts selected may depend on the desired downstream applications of the formed polymer resins, such for film, blow-molding applications, pipe applications, and so forth.

Generally, the mixed catalyst system provides a polymer with a mix of beneficial properties as a result of a carefully tailored combination of molecular weight distribution and the composition distribution. The ability to control the molecular weight distribution (MWD) and the composition distribution (CD) of the system is typically vital in determining the processability and strength of the resultant polymer.

These factors can be adjusted by controlling the MWD, which, in turn, can be adjusted by changing the relative amount of the combination of pre-catalysts on the support. This may be adjusted during the formation of the pre-catalysts, for example, by supporting the three, or more, catalysts on a single support. In some embodiments, the relative amounts of the pre-catalysts can be adjusted by adding one of the components as trim to a catalyst mixture en-route to the reactor. Feedback of polymer property data can be used to control the amount of catalyst addition.

In sum, certain embodiments provide a polymerization system, method, and catalyst system for producing polyethylene. The techniques include polymerizing ethylene in the presence of a catalyst system in a reactor to form the polyethylene, wherein the catalyst system has a first catalyst such as metallocene catalyst, and a second catalyst such as another metallocene catalyst or a non-metallocene catalyst. The reactor conditions and an amount of the second catalyst (or ratio of second catalyst to first catalyst) fed to the reactor may be adjusted to control melt index (MI) (I-2) and density of the polyethylene based on a target melt flow ratio (MFR) (I-21/I-2) and a desired combination of MWD and CD. The reactor conditions adjusted may be operating temperature of the reactor, a comonomer concentration and/or hydrogen concentration in the polymerization mixture in the reactor, and the like. The reactant concentrations may be adjusted to meet a MI target and/or density target of the polyethylene, for example, at a given MFR range of the polyethylene. In examples, the MI (I-2) of the polyethylene is in a range from 0.5 to 1.0 dg/min, and the density of the polyethylene is in a range from 0.916 to 0.926 g/cm3

In some embodiments, the first catalyst includes the metallocene catalyst HfP, and the second catalyst is the metallocene Eth-Ind. Further, the catalyst system may be a common-supported catalyst system. Moreover, the second catalyst may be added as a trim catalyst to a slurry having the first catalyst fed the reactor. The first catalyst and the second catalyst may be impregnated on a single support. Furthermore, in certain embodiments, the first catalyst promotes polymerization of the ethylene into a high molecular-weight portion of the polyethylene, and the second catalyst promotes polymerization of the ethylene into a low molecular-weight portion of the polyethylene. Again, an amount of the second catalyst fed (or the catalyst trim ratio) to the polymerization reactor may be adjusted along with reactor conditions to control polyolefin properties at a given MFR, for instance.

Other embodiments provide for a system and method of producing polyethylene, including: polymerizing ethylene in presence of a catalyst system in a reactor to form polyethylene, wherein the catalyst system comprises a first catalyst and a second catalyst; and adjusting reactor temperature, reactor hydrogen concentration, and an amount of the second catalyst fed to the reactor, to give a range of melt flow ratio (MFR) of the polyethylene while maintaining density and melt index (MI) of the polyethylene. An initial amount of the second catalyst may be co-deposited with first catalyst prior to being fed to the reactor. The adjusted amount of the second catalyst fed to the reactor may be the catalyst trim ratio. In certain embodiments, the first catalyst promotes polymerization of the ethylene into a high molecular-weight portion of the polyethylene, and wherein the second catalyst promotes polymerization of the ethylene into a low molecular-weight portion of the polyethylene. In some embodiments, control of MI is substantially decoupled from control of MFR. In particular embodiments, the reactor hydrogen concentration as a ratio of hydrogen to ethylene in the reactor is a primary control variable for MI, a ratio of comonomer (e.g., 1-hexene) to ethylene in the reactor is a primary control variable for the density, and the reactor temperature and the amount of the second catalyst fed to the reactor as a catalyst trim ratio are primary control variables of the MFR. In examples, the MFR is in the range of 20 to 45, the density is in the range of 0.912 to 0.940, and the MI is in the range of 0.1 dg/10 min to 100 dg/10 min.

Yet other embodiments provide for a system and method of producing polyethylene, including: polymerizing ethylene in presence of a catalyst system in a reactor to form polyethylene, wherein the catalyst system comprises a first catalyst and a second catalyst; and adjusting reactor conditions and an amount of the second catalyst fed to the reactor, to accommodate a range of melt index (MI).

Various catalyst systems and components may be used to generate the polymers and molecular weight compositions disclosed. These are discussed in the sections to follow. The first section discusses catalyst compounds that can be used in embodiments, including the first metallocene and the second metallocene catalysts, among others. The second section discusses generating catalyst slurries that may be used for implementing the techniques described. The third section discusses supports that may be used. The fourth section discusses catalyst activators that may be used. The fifth section discusses the catalyst component solutions that may be used to add additional catalysts in trim systems. Gas phase polymerizations may use static control or continuity agents, which are discussed in the fifth section. A gas-phase polymerization reactor with a trim feed system is discussed in the sixth section. The use of the catalyst composition to control product properties is discussed in a sixth section and an exemplary polymerization process is discussed in the seventh section. Examples of the implementation of the procedures discussed in incorporated into an eighth section.

Catalyst Compounds

Metallocene Catalyst Compounds

Metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring system(s), at least a portion of which includes π-bonded systems, such as cycloalkadienyl ligands and heterocyclic analogues. The ring(s) or ring system(s) typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H4 Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one exemplary embodiment; and selected from the group consisting of Groups 3 through 10 atoms in a more particular exemplary embodiment; and selected from the group consisting of Sc, Ti, Zr, Hf, V, Nb, Ta, Mn, Re, Fe, Ru, Os, Co, Rh, Ir, and Ni in yet a more particular exemplary embodiment; and selected from the group consisting of Groups 4, 5, and 6 atoms in yet a more particular exemplary embodiment; and Ti, Zr, Hf atoms in yet a more particular exemplary embodiment; and Zr in yet a more particular exemplary embodiment. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the structure (VI):
CpACpBMXn,
in which M is as described above; each X is chemically bonded to M; each Cp group is chemically bonded to M; and n is 0 or an integer from 1 to 4, and either 1 or 2 in a particular exemplary embodiment.

The ligands represented by CpA and CpB in structure (VI) can be the same or different cyclopentadienyl ligands or ligands isolobal to cyclopentadienyl, either or both of which can contain heteroatoms and either or both of which can be substituted by a group R. In at least one specific embodiment, CpA and CpB are independently selected from the group consisting of cyclopentadienyl, indenyl, tetrahydroindenyl, fluorenyl, and substituted derivatives of each.

Independently, each CpA and CpB of structure (VI) can be unsubstituted or substituted with any one or combination of substituent groups R. Non-limiting examples of substituent groups R as used in structure (VI) as well as ring substituents in structures discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. More particular non-limiting examples of alkyl substituents R associated with structures (VI) through (XI) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each leaving group, or X, in the structure (VI) above and for the structures in (VII) through (IX) below is independently selected from the group consisting of: halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C8 alkylaryloxys, C1 to C12 fluoroalkyls, C6 to C12 fluoroaryls, and C1 to C12 heteroatom-containing hydrocarbons and substituted derivatives thereof, in a more particular exemplary embodiment; hydride, halogen ions, C1 to C6 alkyls, C2 to C6 alkenyls, C7 to C18 alkylaryls, C1 to C6 alkoxys, C6 to C14 aryloxys, C7 to C16 alkylaryloxys, C1 to C6 alkylcarboxylates, C1 to C6 fluorinated alkylcarboxylates, C6 to C12 arylcarboxylates, C7 to C18 alkylarylcarboxylates, C1 to C6 fluoroalkyls, C2 to C6 fluoroalkenyls, and C7 to C18 fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; C1 to C12 alkyls, C2 to C12 alkenyls, C6 to C12 aryls, C7 to C20 alkylaryls, substituted C1 to C12 alkyls, substituted C6 to C12 aryls, substituted C7 to C20 alkylaryls and C1 to C12 heteroatom-containing alkyls, C1 to C12 heteroatom-containing aryls, and C1 to C12 heteroatom-containing alkylaryls, in yet a more particular exemplary embodiment; chloride, fluoride, C1 to C6 alkyls, C2 to C6 alkenyls, C7 to C18 alkylaryls, halogenated C1 to C6 alkyls, halogenated C2 to C6 alkenyls, and halogenated C7 to C18 alkylaryls, in yet a more particular exemplary embodiment; chloride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment.

Other non-limiting examples of X groups include amides, amines, phosphines, ethers, carboxylates, dienes, hydrocarbon radicals having from 1 to 20 carbon atoms, fluorinated hydrocarbon radicals (e.g., —C6F5 (pentafluorophenyl)), fluorinated alkylcarboxylates (e.g., CF3C(O)O—), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more X's form a part of a fused ring or ring system. In at least one specific embodiment, X can be a leaving group selected from the group consisting of chloride ions, bromide ions, C1 to C10 alkyls, and C2 to C12 alkenyls, carboxylates, acetylacetonates, and alkoxides.

The metallocene catalyst compound includes those of structure (VI) where CpA and CpB are bridged to each other by at least one bridging group, (A), such that the structure is represented by structure (VII):

CpA(A)CpBMXn.

These bridged compounds represented by structure (VII) are known as "bridged metallocenes." The elements CpA, CpB, M, X and n in structure (VII) are as defined above for structure (VI); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be C1 to C12 alkyl or aryl substituted to satisfy neutral valency. In at least one specific embodiment, the bridging group (A) can also include substituent groups R as defined above (for structure (VI)) including halogen radicals and iron. In at least one specific embodiment, the bridging group (A) can be represented by C1 t C6 alkylenes, substituted C1 to C6 alkylenes, oxygen, sulfur, R'2C=, R'2Si=, =Si(R')2Si(R'2)=, R'2Ge=, and R'P=, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of structure (VII) includes two or more bridging groups (A). In one or more embodiments, (A) can be a divalent bridging group bound to both CpA and CpB selected from the group consisting of divalent C1 to C20 hydrocarbyls and C1 to C20 heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, Cl). The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands CpA and CpB of structure (VI) and (VII) can be different from each other. The ligands CpA and CpB of structure (VI) and (VII) can be the same. The metallocene catalyst compound can include bridged mono-ligand metallocene compounds (e.g., mono cyclopentadienyl catalyst components).

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The amount of the transition metal component of the one or more metallocene catalyst compounds in the catalyst system can range from a low of about 0.2 wt. %, about 3 wt. %, about 0.5 wt. %, or about 0.7 wt. % to a high of about 1 wt. %, about 2 wt. %, about 2.5 wt. %, about 3 wt. %, about 3.5 wt. %, or about 4 wt. %, based on the total weight of the catalyst system.

The metallocene catalyst compounds can include any combination of any embodiment discussed and described herein. For example, the metallocene catalyst compound can include, but is not limited to, bis(n-butylcyclopentadienyl) zirconium $(CH_3)_2$, bis(n-butylcyclopentadienyl) zirconium Cl2, bis(n-butylcyclopentadienyl) zirconium Cl2, (n-propylcyclopentadienyl, tetramethylcyclopentadienyl) zirconium Cl2, [(pentamethyphenylNCH2CH2)2NH]ZrBn2, [(pentamethylphenylNCH2CH2)2O]ZrBn2, or any combinations thereof. Other metallocene catalyst compounds are contemplated.

Although the catalyst compounds may be written or shown with methyl-, chloro-, or phenyl-leaving groups attached to the central metal, it can be understood that these groups may be different without changing the catalyst involved. For example, each of these ligands may independently be a benzyl group (Bn), a methyl group (Me), a chloro group (Cl), a fluoro group (F), or any number of other groups, including organic groups, or heteroatom groups. Further, these ligands will change during the reaction, as a pre-catalyst is converted to the active catalyst for the reaction.

Group 15 Atom and Non-Metallocene Catalyst Compounds

The catalyst system can include one or more Group 15 metal-containing catalyst compounds. As used herein, these are termed non-metallocene catalyst compounds. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a C1 to C20 hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds can be described more particularly with structures (VIII) or (IX):

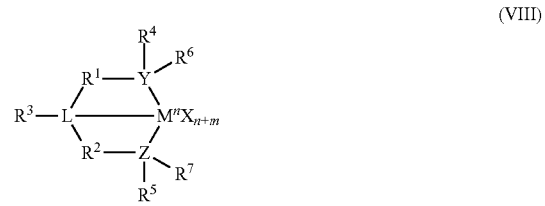

(VIII)

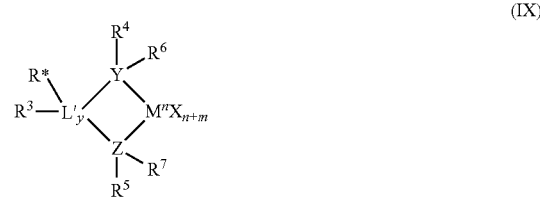

(IX)

where M is a Group 3 to 12 transition metal or a Group 13 or 14 main group metal, a Group 4, 5, or 6 metal. In many embodiments, M is a Group 4 metal, such as zirconium, titanium, or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen or oxygen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. R1 and R2 are, independently, a C1 to C20 hydrocarbon group, a heteroatom containing group having up to twenty carbon atoms, silicon, germanium, tin, lead, or phosphorus. In many embodiments, R1 and R2 are a C2 to C20 alkyl, aryl or aralkyl group, such as a linear, branched or cyclic C2 to C20 alkyl group, or a C2 to C6 hydrocarbon group, such as the X described with respect to structures (VI) and (VII) above. R1 and R2 may also be interconnected to each other. R3 may be absent or may be a hydrocarbon group, a hydrogen, a halogen, a heteroatom containing group. In many embodiments, R3 is absent, for example, if L is an oxygen, or a hydrogen, or a linear, cyclic, or branched alkyl group having 1 to 20 carbon atoms. R4 and R5 are independently an alkyl group, an aryl group, substituted aryl group, a cyclic alkyl group, a substituted cyclic alkyl group, a cyclic aralkyl group, a substituted cyclic aralkyl group, or multiple ring system, often having up to 20 carbon atoms. In many embodiments, R4 and R5 have between 3 and 10 carbon atoms, or are a C1 to C20 hydrocarbon group, a C1 to C20 aryl group or a C1 to C20 aralkyl group, or a heteroatom containing group. R4 and R5 may be interconnected to each other. R6 and R7 are independently absent, hydrogen, an alkyl group, halogen, heteroatom, or a hydrocarbyl group, such as a linear, cyclic or branched alkyl group having 1 to 20 carbon atoms. In many embodiments, R6 and R7 are absent. R* may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "R1 and R2 may also be interconnected" it is meant that R1 and R2 may be directly bound to each other or may be bound to each other through other groups. By "R4 and R5 may also be interconnected" it is meant that R4 and R5 may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, R4 and R5 are independently a group represented by the following structure (X).

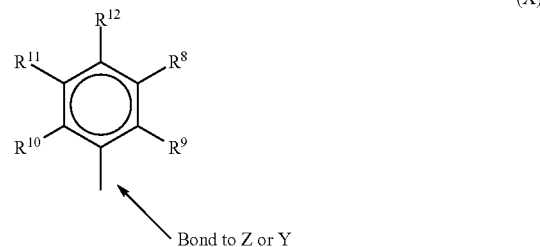

(X)

When $R^4$ and $R^5$ are as formula VII, $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by the following structure (XI).

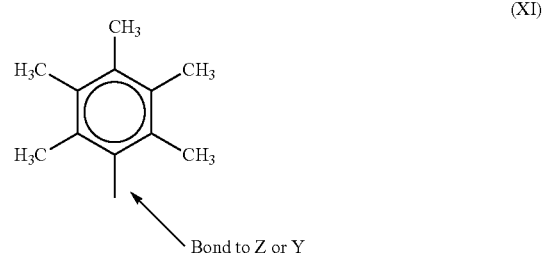

(XI)

When R4 and R5 follow structure (XI), M is a Group 4 metal, such as zirconium, titanium, or hafnium. In many embodiments, M is zirconium. Each of L, Y, and Z may be a nitrogen. Each of R1 and R2 may be —CH2-CH2-. R3 may be hydrogen, and R6 and R7 may be absent. The Group 15 metal-containing catalyst compound can be represented by structure (IV). In formula IV, Ph represents phenyl.

Catalyst Forms

The catalyst system may include a catalyst component in a slurry, which may have an initial catalyst compound, and an added solution catalyst component that is added to the slurry. Generally, the first metallocene catalyst will be supported in the initial slurry, depending on solubility. However, in some embodiments, the initial catalyst component slurry may have no catalysts. In this case, two or more solution catalysts may be added to the slurry to cause each to be supported.

Any number of combinations of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

The catalyst is not limited to a slurry arrangement, as a mixed catalyst system may be made on a support and dried. The dried catalyst system can then be fed to the reactor through a dry feed system.

Support

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include silica, alumina, or a combination thereof. In one embodiment described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for cosupporting solution carried catalysts.

Activator

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as tri (n-butyl)ammonium tetrakis(pentafluorophenyl) boron, a trisperfluorophenyl boron metalloid precursor, a trisperfluoronaphthyl boron metalloid precursor, or any combinations thereof.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Catalyst Component Solution

The catalyst component solution may include only a catalyst compound, such as a metallocene, or may include an activator in addition to the catalyst compound. The catalyst solution used in the trim process can be prepared by dissolving the catalyst compound and optional activators in a liquid solvent. The liquid solvent may be an alkane, such as a C5 to C30 alkane, or a C5 to C10 alkane. Cyclic alkanes such as cyclohexane and aromatic compounds such as toluene may also be used. In addition, mineral oil may be used as a solvent. The solution employed should be liquid under the conditions of polymerization and relatively inert. In one embodiment, the liquid utilized in the catalyst compound solution is different from the diluent used in the catalyst component slurry. In another embodiment, the liquid utilized in the catalyst compound solution is the same as the diluent used in the catalyst component solution.

If the catalyst solution includes both activator and catalyst compound, the ratio of metal in the activator to metal in the catalyst compound in the solution may be 1000:1 to 0.5:1, 300:1 to 1:1, or 150:1 to 1:1. In various embodiments, the activator and catalyst compound are present in the solution at up to about 90 wt. %, at up to about 50 wt. %, at up to about 20 wt. %, preferably at up to about 10 wt. %, at up to about 5 wt. %, at less than 1 wt. %, or between 100 ppm and 1 wt. %, based upon the weight of the solvent and the activator or catalyst compound.

The catalyst component solution can comprises any one of the soluble catalyst compounds described in the catalyst section herein. As the catalyst is dissolved in the solution, a higher solubility is desirable. Accordingly, the catalyst compound in the catalyst component solution may often include a metallocene, which may have higher solubility than other catalysts.

In the polymerization process, described below, any of the above described catalyst component containing solutions may be combined with any of the catalyst component containing slurry/slurries described above. In addition, more than one catalyst component solution may be utilized.

Continuity Additive/Static Control Agent

In gas-phase polyethylene production processes, it may be desirable to use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

in which n may be from about 10 to about 10,000. The polyethyleneimines may be linear, branched, or hyperbranched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[CH2-CH2-NH]— may be used as the polyethyleneimine, materials having primary, secondary, and tertiary branches can also be used. Commercial polyethyleneimine can be a compound having branches of the ethyleneimine polymer.

Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %. Other static control agents are applicable.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Gas Phase Polymerization Reactor

Figure 2:
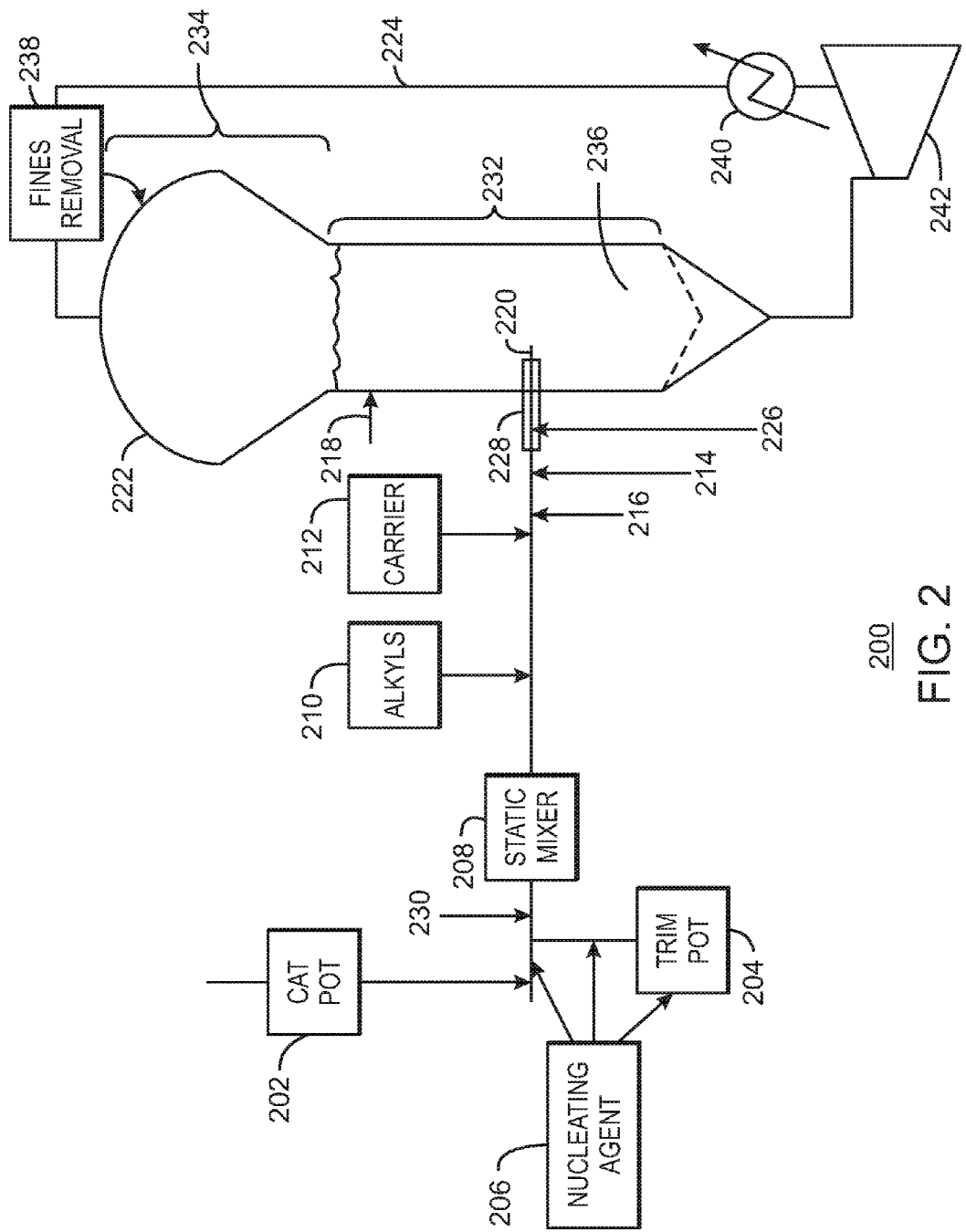
FIG. 2 is a schematic of a gas-phase reactor system, showing the addition of at least two catalysts, at least one of which is added as a trim catalyst in accordance with embodiments described herein.

FIG. 2 is a schematic of a gas-phase reactor system 200, showing the addition of at least two catalysts, at least one of which is added as a trim catalyst. The catalyst component slurry, preferably a mineral oil slurry including at least one support and at least one activator, at least one supported activator, and optional catalyst compounds may be placed in a vessel or catalyst pot (cat pot) 202. In one embodiment, the cat pot 202 is an agitated holding tank designed to keep the solids concentration homogenous. A catalyst component solution, prepared by mixing a solvent and at least one catalyst compound and/or activator, is placed in another vessel, which can be termed a trim pot 204. The catalyst component slurry can then be combined in-line with the catalyst component solution to form a final catalyst composition. A nucleating agent 206, such as silica, alumina, fumed silica or any other particulate matter may be added to the slurry and/or the solution in-line or in the vessels 202 or 204. Similarly, additional activators or catalyst compounds may be added in-line. For example, a second catalyst slurry that includes a different catalyst may be introduced from a second cat pot. The two catalyst slurries may be used as the catalyst system with or without the addition of a solution catalyst from the trim pot.

The catalyst component slurry and solution can be mixed in-line. For example, the solution and slurry may be mixed by utilizing a static mixer 208 or an agitating vessel (not shown). The mixing of the catalyst component slurry and the catalyst component solution should be long enough to allow the catalyst compound in the catalyst component solution to disperse in the catalyst component slurry such that the catalyst component, originally in the solution, migrates to the supported activator originally present in the slurry. The combination forms a uniform dispersion of catalyst compounds on the supported activator forming the catalyst composition. The length of time that the slurry and the solution are contacted is typically up to about 220 minutes, such as about 1 to about 60 minutes, about 5 to about 40 minutes, or about 10 to about 30 minutes.

When combining the catalysts, the activator and the optional support or additional co-catalysts, in the hydrocarbon solvents immediately prior to a polymerization reactor it is desirable that the combination yield a new polymerization catalyst in less than 1 h, less than 30 min, or less than 15 min. Shorter times are more effective, as the new catalyst is ready before being introduces into the reactor, providing the potential for faster flow rates.

In another embodiment, an aluminum alkyl, an ethoxylated aluminum alkyl, an aluminoxane, an anti-static agent or a borate activator, such as a C1 to C15 alkyl aluminum (for example tri-isobutyl aluminum, trimethyl aluminum or the like), a C1 to C15 ethoxylated alkyl aluminum or methyl aluminoxane, ethyl aluminoxane, isobutylaluminoxane, modified aluminoxane or the like are added to the mixture of the slurry and the solution in line. The alkyls, antistatic agents, borate activators and/or aluminoxanes may be added from an alkyl vessel 210 directly to the combination of the solution and the slurry, or may be added via an additional alkane (such as isopentane, hexane, heptane, and or octane) carrier stream, for example, from a hydrocarbon vessel 212. The additional alkyls, antistatic agents, borate activators and/or aluminoxanes may be present at up to about 500 ppm, at about 1 to about 300 ppm, at 10 to about 300 ppm, or at about 10 to about 100 ppm. Carrier streams that may be used include isopentane and or hexane, among others. The carrier may be added to the mixture of the slurry and the solution, typically at a rate of about 0.5 to about 60 lbs/hr (27 kg/hr). Likewise a carrier gas 214, such as nitrogen, argon, ethane, propane, and the like, may be added in-line to the mixture of the slurry and the solution. Typically the carrier gas may be added at the rate of about 1 to about 100 lb/hr (0.4 to 45 kg/hr), or about 1 to about 50 lb/hr (5 to 23 kg/hr), or about 1 to about 25 lb/hr (0.4 to 11 kg/hr).

In another embodiment, a liquid carrier stream is introduced into the combination of the solution and slurry that is moving in a downward direction. The mixture of the solution, the slurry and the liquid carrier stream may pass through a mixer or length of tube for mixing before being contacted with a gaseous carrier stream.

Similarly, a comonomer 216, such as hexene, another alpha-olefin, or diolefin, may be added in-line to the mixture of the slurry and the solution. The slurry/solution mixture is then passed through an injection tube 220 to a reactor 222. In some embodiments, the injection tube may aerosolize the slurry/solution mixture. Any number of suitable tubing sizes and configurations may be used to aerosolize and/or inject the slurry/solution mixture.

In one embodiment, a gas stream 226, such as cycle gas, or re-cycle gas 224, monomer, nitrogen, or other materials is introduced into a support tube 228 that surrounds the injection tube 220. To assist in proper formation of particles in the reactor 222, a nucleating agent 218, such as fumed silica, can be added directly into the reactor 222.

When a metallocene catalyst or other similar catalyst is used in the gas phase reactor, oxygen or fluorobenzene can be added to the reactor 222 directly or to the gas stream 226 to control the polymerization rate. Thus, when a metallocene catalyst (which is sensitive to oxygen or fluorobenzene) is used in combination with another catalyst (that is not sensitive to oxygen) in a gas phase reactor, oxygen can be used to modify the metallocene polymerization rate relative to the polymerization rate of the other catalyst. An example of such a catalyst combination is bis(n-propyl cyclopentadienyl)zirconium dichloride and [(2,4,6-Me3C6H2)NCH2CH2]2NHZrBn2, where Me is methyl or bis(indenyl)zirconium dichloride and [(2,4,6-Me3C6H2)NCH2CH2]2NHHfBn2, where Me is methyl. For example, if the oxygen concentration in the nitrogen feed is altered from 0.1 ppm to 0.5 ppm, significantly less polymer from the bisindenyl ZrCl2 will be produced and the relative amount of polymer produced from the [(2,4,6-Me3C6H2)NCH2CH2]2NHHfBn2 is increased. WO 1996/009328 discloses the addition of water or carbon dioxide to gas phase polymerization reactors, for example, for similar purposes. In one embodiment, the contact temperature of the slurry and the solution is in the range of from 0° C. to about 80° C., from about 0° C. to about 60° C., from about 10° C., to about 50° C., and from about 20° C. to about 40° C.

The example above is not limiting, as additional solutions and slurries may be included. For example, a slurry can be combined with two or more solutions having the same or different catalyst compounds and or activators. Likewise, the solution may be combined with two or more slurries each having the same or different supports, and the same or different catalyst compounds and or activators. Similarly, two or more slurries combined with two or more solutions, preferably in-line, where the slurries each comprise the same or different supports and may comprise the same or different catalyst compounds and or activators and the solutions comprise the same or different catalyst compounds and or activators. For example, the slurry may contain a supported activator and two different catalyst compounds, and two solutions, each containing one of the catalysts in the slurry, are each independently combined, in-line, with the slurry.

Use of Catalyst Composition to Control Product Properties

The properties of the product polymer may be controlled by adjusting the timing, temperature, concentrations, and sequence of the mixing of the solution, the slurry and any optional added materials (nucleating agents, catalyst compounds, activators, etc) described above. The MWD, MI, density, MFR, relative amount of polymer produced by each catalyst, and other properties of the polymer produced may also be changed by manipulating process parameters. Any number of process parameters may be adjusted, including manipulating hydrogen concentration in the polymerization system, changing the amount of the first catalyst in the polymerization system, changing the amount of the second catalyst in the polymerization system. Other process parameters that can be adjusted include changing the relative ratio of the catalyst in the polymerization process (and optionally adjusting their individual feed rates to maintain a steady or constant polymer production rate). The concentrations of reactants in the reactor 222 can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further process parameters including concentration parameters that can be adjusted include changing the polymerization temperature, changing the ethylene partial pressure in the polymerization process, changing the ethylene to comonomer ratio in the polymerization process, changing the activator to transition metal ratio in the activation sequence. Time dependent parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one embodiment, the MWD of the polymer product is measured at regular intervals and one of the above process parameters, such as temperature, catalyst compound feed rate, the ratios of the two or more catalysts to each other, the ratio of comonomer to monomer, the monomer partial pressure, and or hydrogen concentration, is altered to bring the composition to the desired level, if necessary. The MWD may be measured by size exclusion chromatography (SEC), e.g., gel permeation chromatography (GPC), among other techniques.

In one embodiment, a polymer product property is measured in-line and in response the ratio of the catalysts being combined is altered. In one embodiment, the molar ratio of the catalyst compound in the catalyst component slurry to the catalyst compound in the catalyst component solution, after the slurry and solution have been mixed to form the final catalyst composition, is 500:1 to 1:500, or 100:1 to 1:100, or 50:1 to 1:50 or 40:1 to 1:10. In another embodiment, the molar ratio of a Group 15 catalyst compound in the slurry to a ligand metallocene catalyst compound in the solution, after the slurry and solution have been mixed to form the catalyst composition, is 500:1, 100:1, 50:1, 10:1, or 5:1. The product property measured can include the dynamic shear viscosity, flow index, melt index, density, MWD, comonomer content, and combinations thereof. In another embodiment, when the ratio of the catalyst compounds is altered, the introduction rate of the catalyst composition to the reactor, or other process parameters, is altered to maintain a desired production rate.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes. In embodiments that use other techniques besides gas phase polymerization, modifications to a catalyst addition system that are similar to those discussed with respect to FIG. 2 can be used. For example, a trim system may be used to feed catalyst to a loop slurry reactor for polyethylene copolymer production.

The terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, or at least 95 wt. % ethylene-derived units. The polyethylene polymers described herein are generally copolymer, but may also include terpolymers, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like.

Referring again to FIG. 2, the fluidized bed reactor 222 can include a reaction zone 232 and a velocity reduction zone 234. The reaction zone 232 can include a bed 236 that includes growing polymer particles, formed polymer particles and a minor amount of catalyst particles fluidized by the continuous flow of the gaseous monomer and diluent to remove heat of polymerization through the reaction zone. Optionally, some of the re-circulated gases 224 can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone 232 can be passed to the velocity reduction zone 234 where entrained particles are removed, for example, by slowing and falling back to the reaction zone 232. If desired, finer entrained particles and dust can be removed in a separation system 238, such as a cyclone and/or fines filter. The gas 224 can be passed through a heat exchanger 240 where at least a portion of the heat of polymerization can be removed. The gas can then be compressed in a compressor 242 and returned to the reaction zone 232. Additional reactor details and means for operating the reactor 222 are described in, for example, U.S. Pat. Nos. 3,709,853; 4,003,712; 4,011,382; 4,302,566; 4,543,399; 4,882,400; 5,352,749; and 5,541,270; EP 0802202; and Belgian Patent No. 839,380.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Thus, the upper temperature limit in one embodiment is the melting temperature of the polyethylene copolymer produced in the reactor. However, higher temperatures may result in narrower MWDs, which can be improved by the addition of structure (IV), or other co-catalysts, as described herein.

Hydrogen gas can be used in olefin polymerization to control the final properties of the polyolefin, such as described in the "Polypropylene Handbook," at pages 76-78 (Hanser Publishers, 1996). Using certain catalyst systems, increasing concentrations (partial pressures) of hydrogen can increase a flow index such as MI of the polyethylene copolymer generated. The MI can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired MI of the final polyolefin polymer. For example, the mole ratio of hydrogen to total monomer (H2:monomer) can be greater than about 0.0001, greater than about 0.0005, or greater than about 0.001. Further, the mole ratio of hydrogen to total monomer (H2:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm, based on weight. Further, the ratio of hydrogen to total monomer (H2:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one embodiment, a hexane, isopentane, or isobutane medium can be employed. The slurry can be circulated in a continuous loop system.

A number of tests can be used to compare resins from different sources, catalyst systems, and manufacturers. Such tests can include melt index, high load melt index, melt index ratio, density, dies swell, environmental stress crack resistance, and many others. Results of tests runs on resins made in embodiments described herein are presented in the examples section.

The product polyethylene can have a melt index ratio (MIR or I21/I2) ranging from about 10 to less than about 300, or, in many embodiments, from about 15 to about 150. Flow index (FI, HLMI, or I21 can be measured in accordance with ASTM D1238 (190° C., 21.6 kg). The melt index (MI, I2) can be measured in accordance with ASTM D1238 (at 190° C., 2.16 kg weight).

Density can be determined in accordance with ASTM D-792. Density is expressed as grams per cubic centimeter (g/cm3) unless otherwise noted. The polyethylene can have a density ranging from a low of about 0.89 g/cm3, about 0.90 g/cm3, or about 0.91 g/cm3 to a high of about 0.95 g/cm3, about 0.96 g/cm3, or about 0.97 g/cm3. The polyethylene can have a bulk density, measured in accordance with ASTM D1895 method B, of from about 0.25 g/cm3 to about 0.5 g/cm3. For example, the bulk density of the polyethylene can range from a low of about 0.30 g/cm3, about 0.32 g/cm3, or about 0.33 g/cm3 to a high of about 0.40 g/cm3, about 0.44 g/cm3, or about 0.48 g/cm3.

The polyethylene can be suitable for such articles as films, fibers, nonwoven and/or woven fabrics, extruded articles, and/or molded articles. Examples of films include blown or cast films formed in single layer extrusion, coextrusion, or lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions by injection molding or rotation molding or blow molding processes in the form of bottles, tanks, large hollow articles, rigid food containers and toys, etc.

Data for example BOCD polymers are presented in Tables 1b, 2a, and 2b. Data for selected comparative conventional polymers are given in Table 2c. These tables are discussed in more detail throughout the discussion below.

Table 1b is a summary of production and property data with respect to example BOCD polymers. Table 1b data as generated may be representative of a technique in which a target or desired different MFR's for various polymers are selected or specified. (See also FIGS. 5A, 5B, and 6 for exemplary graphical representations of such a technique.) To achieve the selected target MFR for a given polymer, the polymerization reactor temperature and an amount of a second (trim) catalyst to feed to the reactor the reactor are adjusted or specified. To maintain the same or similar density and MI through the range of MFR's for the various polymers, the comonomer amount or ratio to monomer (e.g., 1-hexene/ethylene or butene/ethylene) and the hydrogen amount or ratio to monomer (e.g., hydrogen/ethylene) in the reactor feed or in the polymerization mixture in the reactor may be adjusted (selected or specified).

For instance, polymer A0 was produced at a reactor temperature of 86° C. and with no second or trim catalyst to give a polymer MFR of 21. The similar polymer A0-R was reproduced. Then, polymer A1 produced at the same reactor temperature of 86° C. but with the addition of a second or time catalyst to give a higher MFR of 29. To maintain the density and MI substantially the same, respectively, the 1-hexene/ethylene and hydrogen/ethylene ratios are adjusted. Such a technique may be repeated through a range of MFRs, as indicated in Table 1b. It should be noted for some of the polymers, the reactor temperature is lower from 86° C. to 80° C. to give an increased MFR of the polymer. Moreover, an adjustment may be to change to comonomer type, such as changing from 1-hexene to butene. Of course, other adjustments with respect to operating variables and materials may be made for a variety of MFR targets over desired density and MI. Lastly, Table 1b demonstrates that MFR may be "decoupled" from MI.

TABLE 1b

Summary
Independent Control of MI/MFR

| Product Description | BTEC Density | BTEC MI (I2) | BTEC MFR (I21/I2) | Rxtr Tmp (Deg C.) | C2 P-P (psia) | Trim (Calc Flow g/hr) | C6/C2 (mol ratio) | C4/C2 (ratio) | H2/C2 (PPM/Mol %) |
|---|---|---|---|---|---|---|---|---|---|
| *Coreset* | | | | | | | | | |
| A0 | 0.918 | 1.1 | 21 | 86 | 220 | | 0.0140 | | 7.00 |
| A0-R | 0.919 | 1.0 | 22 | 86 | 220 | | 0.0140 | | 7.00 |
| A1 | 0.920 | 0.9 | 29 | 86 | 220 | 61.7 | 0.0167 | | 7.50 |
| A2 | 0.922 | 0.9 | 36 | 86 | 220 | 99.6 | 0.0190 | | 7.93 |
| B0 | 0.919 | 1.1 | 27 | 80 | 220 | | 0.0152 | | 7.11 |
| B1 | 0.919 | 0.9 | 37 | 80 | 220 | 40.1 | 0.0172 | | 7.10 |
| B2 | 0.922 | 0.9 | 59 | 80 | 220 | 72.9 | 0.0192 | | 6.87 |
| *Branched out from coreset for different MI/Density/Comonomer Type* | | | | | | | | | |
| A1-b | 0.917 | 0.8 | 26 | 86 | 220 | 44.0 | 0.0183 | | 7.35 |
| A1-c | 0.927 | 0.8 | 26 | 86 | 220 | 58.1 | 0.0130 | | 4.70 |
| A2-b | 0.920 | 1.0 | 37 | 86 | 220 | 111.5 | | 0.0727 | 8.54 |
| B1-b | 0.919 | 0.7 | 37 | 80 | 220 | 43.0 | 0.0175 | | 7.00 |
| B1-c | 0.925 | 0.9 | 36 | 80 | 220 | 49.9 | 0.0152 | | 5.03 |
| B1-d | 0.921 | 0.8 | 38 | 80 | 220 | 125.0 | | 0.0600 | 7.70 |
| B2-b-A | 0.930 | 0.5 | 41 | 80 | 220 | 129.1 | 0.0161 | | 3.20 |
| B2-b-B | 0.932 | 0.6 | 50 | 80 | 220 | 298.9 | 0.0190 | | 3.21 |

TABLE 2a

Summary of Cryo-CFC Analysis with Equal Halves for Core-set

| | | Coreset | | | | | | |
|---|---|---|---|---|---|---|---|---|
| Sample ID | | A0 | A0-R | A1 | A2 | B0 | B1 | B2 |
| Density | (g/cm3) | 0.918 | 0.919 | 0.920 | 0.922 | 0.919 | 0.919 | 0.922 |
| I-2 | (dg/min) | 1.1 | 1.0 | 0.9 | 0.9 | 1.1 | 0.9 | 0.9 |
| MFR | (I-21/I-2) | 21 | 22 | 29 | 36 | 27 | 37 | 59 |
| (log(Mw1) − log(Mw2))/(Tw1 − Tw2) | | −0.0166 | −0.0189 | −0.0190 | −0.0196 | −0.0191 | −0.0203 | −0.0222 |
| Mw1/Mw2 | | 2.04 | 2.17 | 2.74 | 3.27 | 2.94 | 3.73 | 4.53 |
| Tw1 − Tw2 | (° C.) | −18.7 | −17.8 | −23.1 | −26.3 | −24.5 | −28.2 | −29.6 |

TABLE 2b

Summary of Cryo-CFC Analysis with Equal Halves for Branched-out

| | | Branched out from corset | | | | | | | |
|---|---|---|---|---|---|---|---|---|---|
| Sample ID | | A1-b | A1-c | A2-b | B1-b | B1-c | B1-d | B2-b-A | B2-b-B |
| Density | (g/cm3) | 0.917 | 0.927 | 0.920 | 0.919 | 0.925 | 0.921 | 0.930 | 0.932 |
| I-2 | (dg/min) | 0.8 | 0.8 | 1.0 | 0.7 | 0.9 | 0.8 | 0.5 | 0.6 |
| MFR | (I-21/I-2) | 26 | 26 | 37 | 37 | 36 | 38 | 41 | 50 |
| (log(Mw1) − log(Mw2))/(Tw1 − Tw2) | | −0.0165 | −0.0219 | −0.0188 | −0.0205 | −0.0230 | −0.0190 | −0.0264 | −0.0279 |
| Mw1/Mw2 | | 2.62 | 2.47 | 3.88 | 3.85 | 3.23 | 3.65 | 3.51 | 3.32 |
| Tw1 − Tw2 | (° C.) | −25.3 | −18.0 | −31.4 | −28.6 | −22.2 | −29.6 | −20.7 | −18.7 |

TABLE 2c

Summary of Cryo-CFC Analysis with Equal Halves for Comparative Samples

| | | Exceed 1018CA | Exceed 1327CA | Enable 2010CH | Enable 2705CH | LL3201.69 | LD071.LR |
|---|---|---|---|---|---|---|---|
| Density | (g/cm3) | 0.919 | 0.928 | 0.920 | 0.928 | 0.927 | 0.924 |
| I-2 | (dg/min) | 1.0 | 1.3 | 0.9 | 0.5 | 0.9 | 0.7 |
| MFR | (I-21/I-2) | 15 | 15 | 32 | 45 | 25 | 65 |
| (log(Mw1) − log(Mw2))/(Tw1 − Tw2) | | −0.0049 | −0.0032 | 0.0224 | 0.0212 | 0.0114 | 0.0392 |
| Mw1/Mw2 | | 1.14 | 1.07 | 0.78 | 0.87 | 0.53 | 0.36 |
| Tw1 − Tw2 | (° C.) | −11.4 | −9.1 | 4.9 | −2.8 | −24.1 | −11.3 |

Measuring Tw1, Tw2, Mw1 & Mw2 from CFC

A new technique has been developed for determining both MWD and SCBD compositional information, using cross fractionation (CFC), to compare experimental polymers to competitive products on the market. The values Tw1, Tw2, Mw1 & Mw2 may be derived from the CFC data file as reported from the instrument software. In the section of "Fraction summary" in the CFC data file, each fraction is listed by its fractionation temperature (Ti) along with its normalized wt. % value (Wi), cumulative wt. %, i.e., Sum wt. and various moments of molecular weight averages (including Mwi).

Figure 3A:
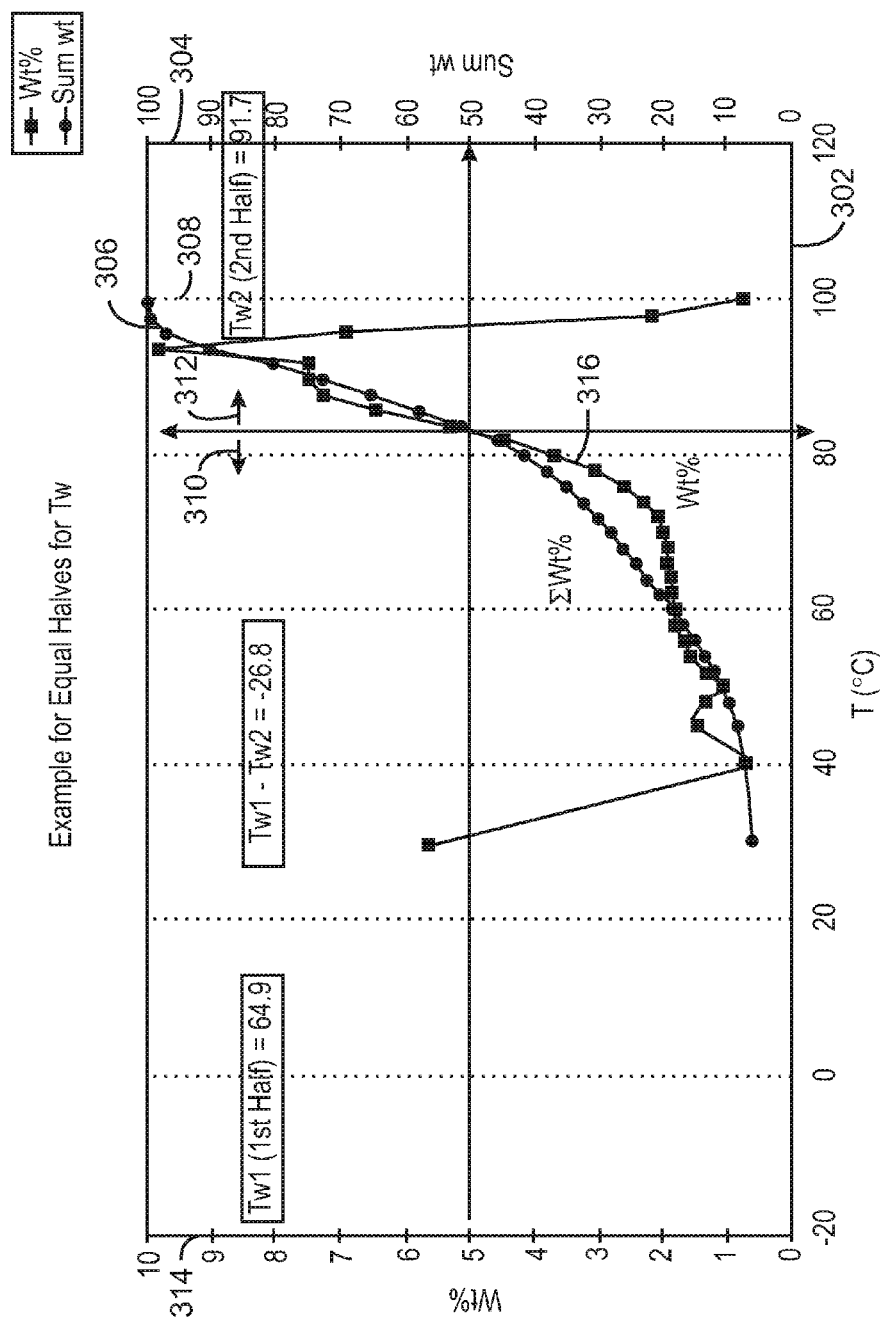
FIGS. 3A and 3B are plots that illustrate the calculations used to determine a CFC result in accordance with embodiments described herein.
Figure 3B:
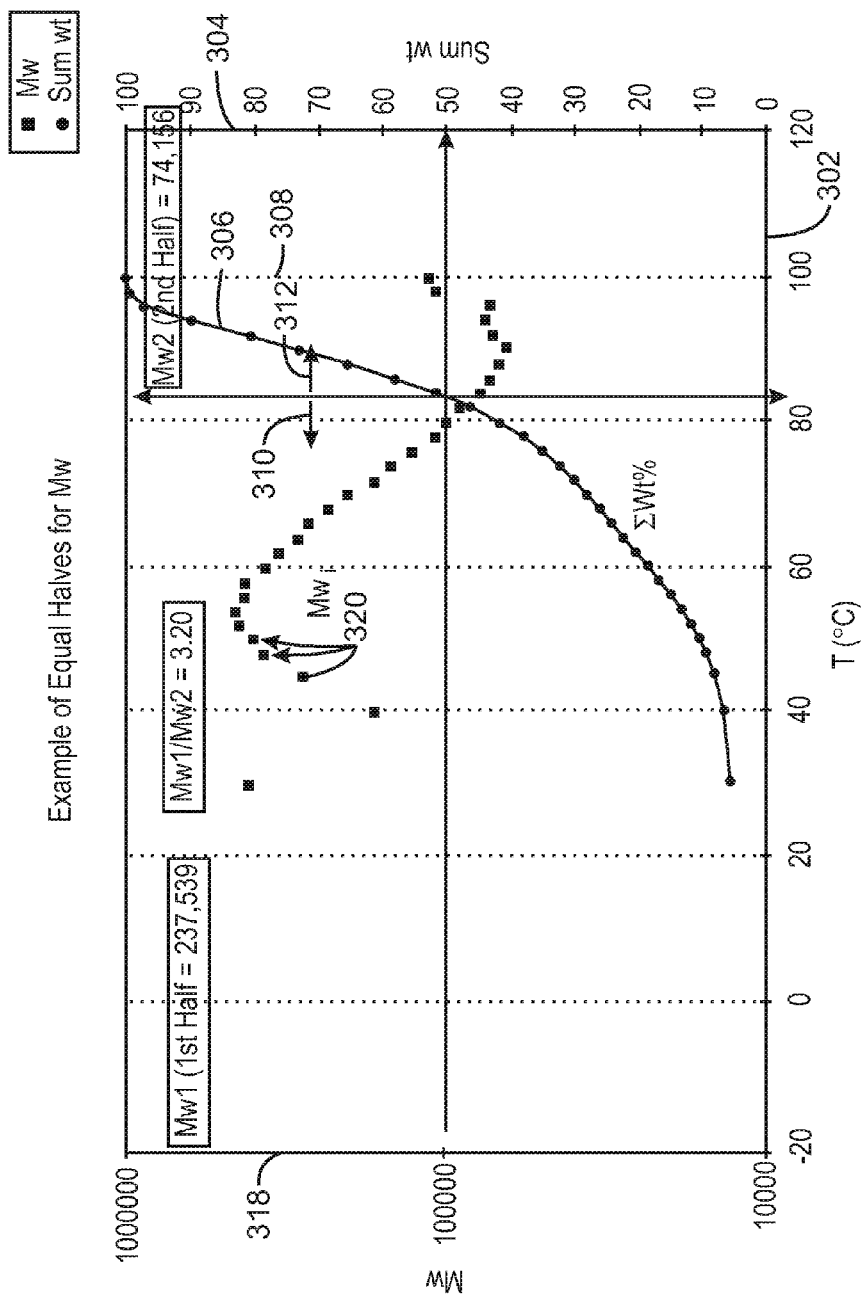

FIGS. 3A and 3B are plots that graphically represent calculations used to determine the CFC result. Fractions having MWD data are considered. In both FIGS. 3A and 3B, the x-axis 302 is the elution temperature in centigrade, while the right hand y-axis 304 is the value of the integral 306 of the molecular weights eluted. The temperature 308 at which 100% of the material has eluted in this example is about 100° C. The point at which 50% of the polymer has eluted is determined by the integral 306, which is used to divide each of the plots into a lower half 310 and an upper half 312.

The values Tw1, Tw2, Mw1 & Mw2 in FIGS. 3A and 3B are derived from the CFC data file as reported from the instrument software. In the section of "Fraction summary" in the CFC data file, each fraction is listed by its fractionation temperature ($T_i$) along with its normalized wt. % value ($W_i$), cumulative wt. %, i.e., Sum wt. on FIGS. 3A and 3B, and various moments of molecular weight averages (including $Mw_i$).

To calculate values of Tw1, Tw2, Mw1 & Mw2, the data in "Fraction summary" was divided into two roughly equal halves. Weight averages of $T_i$ and $Mw_i$ for each half were calculated according to the conventional definition of weight average. Fractions which did not have sufficient quantity (i.e., <0.5 wt. %) to be processed for molecular weight averages in the original data file were excluded from the calculation of Tw1, Tw2, Mw1 & Mw2.

The first part of the process is illustrated by FIG. 3A. From the section of fraction summary in the CFC data file, the fraction whose cumulative wt. % (i.e., Sum wt) is closest to 50 is identified (e.g., the fraction at 84° C. on FIG. 3A). The Fraction summary data is divided into two halves, e.g., Ti<=84° C. as the $1^{st}$ half and Ti>84° C. as the $2^{nd}$ half on FIG. 3A. Fractions which do not have molecular weight averages reported in the original data file are excluded, e.g., excluding the fractions with Ti between 25° C. and 40° C. on FIG. 3A.

In FIG. 3A, the left hand y-axis 310 represents the wt % 312 of the eluted fraction. Using the procedure above to divide the curves into two halves, these values are used to calculate the weight average elution temperature for each half using the formula shown in Eqn. 1.

$$Tw = \frac{\Sigma T_i W_i}{\Sigma W_i} \qquad \text{Eqn. 1}$$

In Eqn. 1, Ti represents the elution temperature for each eluted fraction, and Wi represents the normalized weight % (polymer amount) of each eluted fraction. For the example shown in FIG. 3A, this provides a weight average elution temperature of 64.0° C. for the first half, and 91.7° C. for the second half.

In FIG. 3B, the left hand axis 618 represents the weight average molecular weight ($Mw_i$) 320 of each eluted fraction. These values are used to calculate the weight average molecular weight for each half using the formula shown in Eqn. 2.

$$Mw = \frac{\Sigma Mw_i W_i}{\Sigma W_i} \qquad \text{Eqn. 2}$$

In Eqn. 2, $Mw_i$ represents the weight average molecular weight of each eluted fraction, and $W_i$ represents the normalized weight % (polymer amount) of each eluted fraction. For the example shown in FIG. 3B, this provides a weight average molecular weight of about 238,000 for the first half, and about 74,000 for the second half. The values calculated using the techniques described above may be used to classify the MWD×SCBD for BOCD polymers (Tables 2a and 2b) and control polymers (Table 3) as shown in FIG. 4.

Figure 4:
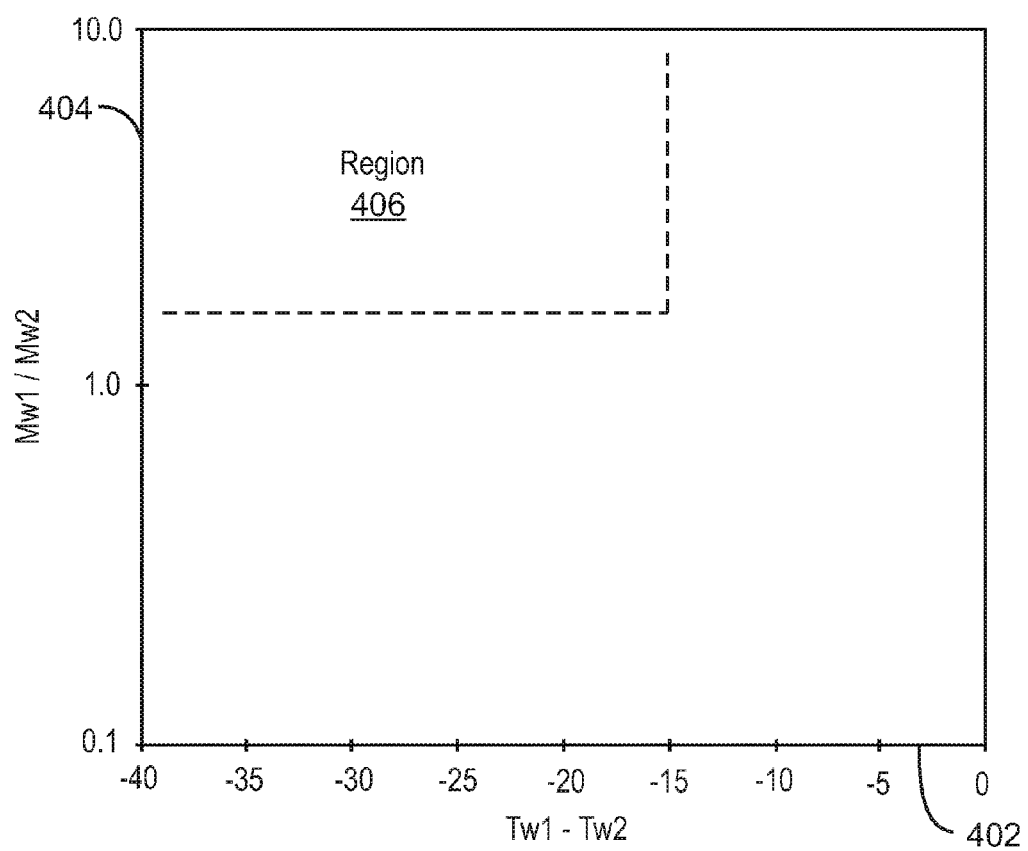
FIG. 4 is a plot of (Mw1/Mw2) vs. (Tw1−Tw2) showing a region of polymers.

FIG. 4 is a semi-log plot 400 of (Mw1/Mw2) vs. (Tw1−Tw2), depicting a region 406 for the polymers listed in Tables 2a and 2b. In the plot 400, the x-axis 402 represents the value of the difference between the first and second weight average elution temperatures. The y-axis 404 in a log scale represents the ratio of the first weight average molecular weight to the second weight average molecular weight. Each of the polymers in Tables 2a and 2b, which also list the calculated values for the weight average molecular weights and the weight average elution temperatures, are represented as falling in region 406. In this illustrated embodiment, the region 406 has a lower bound of 15° C. for Tw1−Tw2, and a lower bound of 2.0 for Mw1/Mw2. That is, in some embodiments, a polyethylene can have a value for Mw1/Mw2 of at least about 2.0, wherein Mw1/Mw2 is a ratio of a Mw1 for a first half of a TREF curve to a Mw2 for a second half of the TREF curve; and a value for Tw1−Tw2 of less than about −15° C., wherein Tw1−Tw2 is a difference of a Tw1 for the first half of the TREF curve to a Tw2 for the second half of the TREF curve.

Polymers that fall in the region 406 may have a broad, orthogonal composition distribution. A BOCD indicates that lower molecular weight polymer chains in the polymer have a high density, e.g., due to a lack of short chain branching (SCB), while higher molecular weight segments have a low density, e.g. due to higher amounts of SCB. In contrast, conventional polymers (e.g., ZN-LLDPE) falling outside of region 406 may generally have longer polymer chains that have a higher density than shorter polymer chains. Such conventional polymers may generally reside on the lower portion of the plot 400.

As can be seen, the newer polymers (Tables 2a, 2b) fall in the region 706 indicating a different MWD and SCBD as compared to the commercial polymers falling outside of region 406. Thus, the use of the technique described above can identify polymers that have BOCDs. Accordingly, the technique can be use both to screen new polymers for the distribution and to control polymer production to target particular locations in the region 706.

Testing Procedure with Cross-Fractionation Chromatography (CFC)

In examples, cross-fractionation chromatography (CFC) was performed on a CFC-2 instrument from Polymer Char, Valencia, Spain. The instrument was operated and subsequent data processing, e.g., smoothing parameters, setting baselines, and defining integration limits, performed according to the manner described in the CFC User Manual provided with the instrument or in a manner commonly used in the art. The instrument was equipped with a TREF column (stainless steel; o.d., ⅜"; length, 15 cm; packing, non-porous stainless steel micro-balls) in the first dimension and a GPC column set (3×PLgel 10 μm Mixed B column from Polymer Labs, UK) in the second dimension. Downstream from the GPC column was an infrared detector (IR4 from Polymer Char) capable of generating an absorbance signal that is proportional to the concentration of polymer in solution.

The sample to be analyzed was dissolved in ortho-dichlorobenzene, at a concentration of about 5 mg/ml, by stirring at 150° C. for 75 min. Then a 0.5-ml volume of the solution containing 2.5 mg of polymer was loaded in the center of the TREF column and the column temperature was reduced and stabilized at ≈120° C. for 30 min. The column was then cooled slowly (0.2° C./min) to 30° C. (for ambient runs) or −15° C. (for cryogenic runs) to crystallize the polymer on the inert support. The low temperature was held for 10 min before injecting the soluble fraction into the GPC column. All GPC analyses were done using solvent ortho-dichlorobenzene at 1 ml/min, a column temperature of 140° C., and in the "Overlap GPC Injections" mode. Then the subsequent higher-temperature fractions were analyzed by increasing the TREF column temperature to the fraction set-points in a stepwise manner, letting the polymer dissolve for 16 min ("Analysis Time"), and injecting the dissolved polymer into the GPC column for 3 min ("Elution Time").

The universal calibration method was used for determining the molecular mass of eluting polymers. Thirteen narrow molecular-weight distribution polystyrene standards (obtained from Polymer Labs, UK) within the range of 1.5-8200 Kg/mol were used to generate a universal calibration curve. Mark-Houwink parameters were obtained from Appendix I of "Size Exclusion Chromatography" by S. Mori and H. G. Barth (Springer). For polystyrene K=1.38×10-4 dl/g and α=0.7; and for polyethylene K=5.05×10-4 dl/g and α=0.693 were used. Fractions having a weight % recovery (as reported by the instrument software) of less than 0.5% were not processed for calculations of molecular-weight averages (Mn, Mw, etc.) of the individual fractions or of aggregates of fractions.

Blown film evaluation data are presented in Tables 3a, 3b, 3c, and 3d. Tables 3a and 3b each compare BOCD polymers A0, A1, and B0 versus conventional polymer Exceed 1018 at low MFR. Tables 3c and 3d each compare BOCD polymers A2, B1, and B2 versus conventional polymer Enable 1020 at high MFR.

TABLE 3a

Blown Film Evaluation of Core-set vs. Exceed at low MFR (1 mil Gauge)

| | | Exceed 1018 CA @ 1 mil | A0 @ 1 mil | A1 @ 1 mil | B0 @ 1 mil |
|---|---|---|---|---|---|
| Density | (g/cm3) | 0.919 | 0.918 | 0.920 | 0.919 |
| MI (I-2) | (dg/min) | 1.0 | 1.1 | 0.9 | 1.1 |
| MFR | (I-21/I-2) | 15 | 21 | 29 | 27 |
| Motor Load | (%) | 64.9 | 60.4 | 54.6 | 52.9 |
| E.S.O. | (lb/HP-hr) | 9.26 | 10.41 | 10.77 | 11.45 |
| MD Modulus | (psi) | 24,625 | 27,302 | 30,883 | 27,360 |
| TD Modulus | (psi) | 27,167 | 33,362 | 40,048 | 32,126 |
| 26" Dart | (g/mil) | 342 | 530 | 702 | 649 |
| Average Mode | (psi) | 25,896 | 30,332 | 35,466 | 29,743 |
| Cal Dart per. U.S. Pat. No. 6,255,426 | (g/mil) | 488 | 294 | 193 | 312 |
| Msrd. Dart vs. U.S. Pat. No. 6,255,426 | (% dif) | 70% | 180% | 364% | 208% |

TABLE 3b

Blown Film Evaluation of Core-set vs. Exceed at low MFR (2 mil gauge)

| | | Exceed 1018 CA @ 2 mil | A0 @ 2 mil | A1 @ 2 mil | B0 @ 2 mil |
|---|---|---|---|---|---|
| Density | (g/cm3) | 0.919 | 0.918 | 0.920 | 0.919 |
| MI (I-2) | (dg/min) | 1.0 | 1.1 | 0.9 | 1.1 |
| MFR | (I-21/I-2) | 15 | 21 | 29 | 27 |
| Motor Load | (%) | 65.1 | 60.7 | 54.1 | 53.0 |
| E.S.O. | (lb/HP-hr) | 9.20 | 10.49 | 10.83 | 11.36 |
| MD Modulus | (psi) | 25,755 | 28,220 | 31,614 | 30,900 |
| TD Modulus | (psi) | 28,183 | 35,834 | 39,665 | 33,534 |
| 26" Dart | (g/mil) | 622 | >655 | >667 | >664 |
| Average Mode | (psi) | 26,969 | 32,027 | 35,640 | 32,217 |
| Cal Dart per. U.S. Pat. No. 6,255,426 | (g/mil) | 426 | 251 | 191 | 247 |
| Msrd. Dart vs. U.S. Pat. No. 6,255,426 | (% dif) | 146% | 279% | 367% | 283% |

TABLE 3c

Blown Film Evaluation of Core-set vs. Enable at high MFR (1 mil gauge)

|  |  | Enable 2010 CH @ 1 mil | A2 @ 1 mil | B1 @ 1 mil | B2 @ 1 mil |
|---|---|---|---|---|---|
| Density | (g/cm3) | 0.920 | 0.922 | 0.919 | 0.922 |
| MI (I-2) | (dg/min) | 0.9 | 0.9 | 0.9 | 0.9 |
| MFR | (I-21/I-2) | 32 | 36 | 37 | 59 |
| Motor Load | (%) | 50.8 | 49.4 | 50.8 | 45.1 |
| E.S.O. | (lb/HP-hr) | 11.75 | 11.49 | 11.23 | 12.34 |
| MD Modulus | (psi) | 27,410 | 35,212 | 33,636 | 33,945 |
| TD Modulus | (psi) | 32,178 | 46,169 | 35,444 | 49,647 |
| 26" Dart | (g/mil) | 185 | 725 | 906 | 533 |
| Average Mode | (psi) | 29,794 | 40,691 | 34,540 | 41,796 |
| Cal Dart per. U.S. Pat. No. 6,255,426 | (g/mil) | 310 | 146 | 206 | 140 |
| Msrd. Dart vs. U.S. Pat. No. 6,255,426 | (% dif) | 60% | 495% | 440% | 380% |

TABLE 3d

Blown Film Evaluation of Core-set vs. Enable at high MFR (2 mil gauge)

|  |  | Enable 2010 CH @ 2 mil | A2 @ 2 mil | B1 @ 2 mil | B2 @ 2 mil |
|---|---|---|---|---|---|
| Density | (g/cm3) | 0.920 | 0.922 | 0.919 | 0.922 |
| I-2 | (dg/min) | 0.9 | 0.9 | 0.9 | 0.9 |
| MFR | (I-21/I-2) | 32 | 36 | 37 | 59 |
| Motor Load | (%) | 50.8 | 49.5 | 50.8 |  |
| E.S.O. | (lb/HP-hr) | 11.91 | 11.48 | 11.27 |  |
| MD Modulus | (psi) | 27,395 | 30,876 | 30,490 |  |
| TD Modulus | (psi) | 30,049 | 41,384 | 38,703 |  |
| 26" Dart | (g/mil) | 258 | 587 | >645 |  |
| Average Mode | (psi) | 28,722 | 36,130 | 34,597 |  |
| Cal Dart per. U.S. Pat. No. 6,255,426 | (g/mil) | 348 | 185 | 205 |  |
| Msrd. Dart vs. U.S. Pat. No. 6,255,426 | (% dif) | 74% | 317% | 342% |  |

Figure 5A:
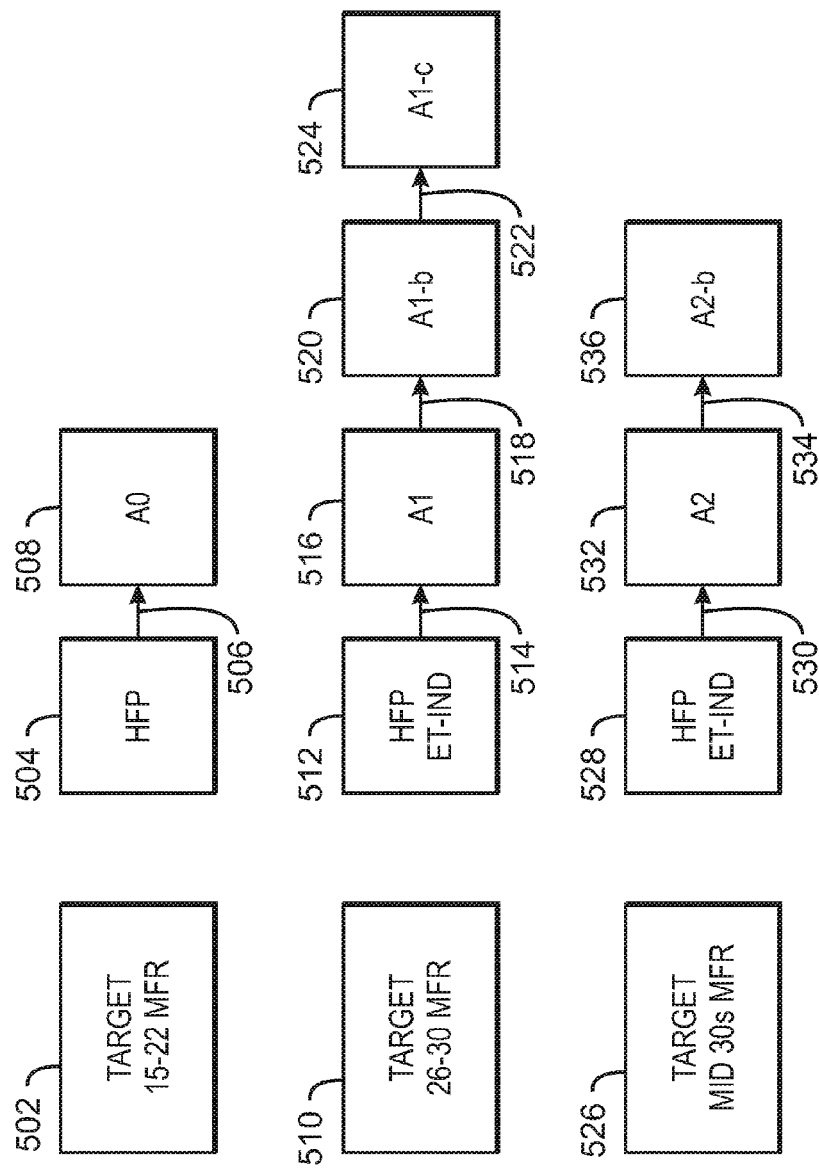

FIG. 5A is a diagrammatical representation of techniques for generating targets or recipes, and producing, some of the exemplary BOCD polymers of Table 1, those listed in Table 2a. The techniques may be to produce various BOCD polymers over a range of polymer MFRs at the same or similar respective polymer density and MI. Such techniques may range from a design of experiments (DOE) for target values of polymerization operating variables and polymer properties, to the control of actual commercial production of the BOCD polymers. In the illustrated embodiment of FIG. 5A, a target MFR range 502 of 15-22 is specified with a chosen reactor temperature (e.g., at 86° C. in Table 1). This is based on the learning from prior experiments for the MFR capability of a single catalyst at various reactor temperatures. As indicated in block 504, the single catalyst system (HfP) in this example is specified with initial polymerization reactor conditions for the target MFR range 502. Adjustments 506 are made to operating variable targets to give polymer A0 508. As indicated above with respect to Table 1, the reactor temperature and amount of any second or trim catalyst may be primary variables for MFR. The comonomer/ethylene ratio, e.g., 1-hexene/ethylene (C6/C2) ratio or butane/ethylene (C4/C2) ratio, may be a primary variable for polymer density. The hydrogen/ethylene (H2/C2) ratio may be a primary variable for polymer MI.

Continuing with FIG. 5A, for a target polymer MFR range 510 of 26-30, a second catalyst (i.e., Et-Ind) is added to the system at the condition of 508 until the MFR target specified by block 512 is reached while MI and density were allowed to float during the transition. After the MFR target in 512 is achieved, operation adjustments 514 are made to give polymer A1 516 with MI & Density target same as 508. Operating adjustments 518 are made to give polymer A1-b 520. Operating adjustments 522 are made to give polymer A1-c 524. With such operation adjustments, one can independently change MI and Density for 516, 520 & 254 while maintaining the MFR in a very tight range of 510. For a target polymer MFR range 526 in the mid-30's, a dual-catalyst system (HfP and Et-Ind) and initial reactor conditions are specified, as reference by block 528. Operating adjustments 530 are made to give polymer A2 532. Operating adjustments 534 are made to give polymer A2-b 536. As discussed, the adjustments 514, 518, 522, 530, and 534 are indicated in Table 1b above.

Figure 5B:
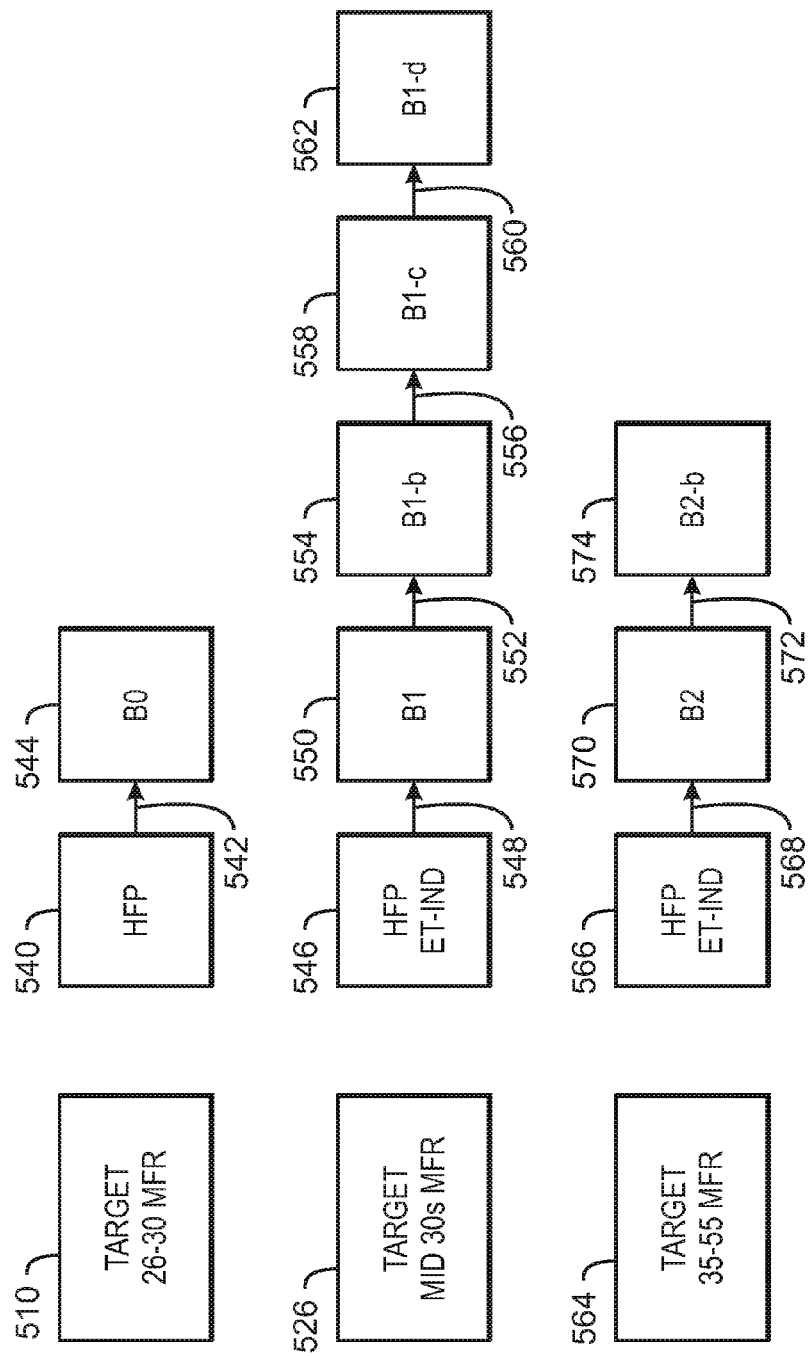
FIG. 5B is a diagrammatical representation of techniques for generating targets or recipes, and producing, some of the exemplary BOCD polymers of Table 1, those listed in Table 2b.

FIG. 5B is similar to FIG. 5A but with different BOCD polymers from Table 1b. FIG. 5B is a diagrammatical representation of techniques for generating targets or recipes, and producing, some of the exemplary BOCD polymers of Table 1b, those listed in Table 2b. Again, such techniques with respect to FIGS. 5A and 5B may be to produce various BOCD polymers over a range of polymer MFRs while maintaining the polymer density and MI. As mentioned, the techniques may range from DOE for target values of polymerization operating variables (e.g., in recipes) and polymer properties, to the control of actual commercial production of the BOCD polymers, and so forth. In the illustrated embodiment of FIG. 5B, at a different chosen reactor temperature (e.g., 80° C. in Table 1b), a different target MFR range 510 of 26-30 is specified for the same single catalyst. As indicated in block 540, the single catalyst system (HfP) in this example is specified with initial polymerization reactor conditions for the target MFR range 510. Adjustments 540 are made to operating variables or operating variable targets to give polymer B0 544. For a target polymer MFR range 526 of mid-30's, a similar procedure as in FIG. 5A from 508 to 512 is followed to reach 546 from 544 of FIG. 5B. Operating adjustments 548 are made to give polymer B1 550. Operating adjustments 552 are made to give polymer B1-b 554. Operating adjustments 556 are made to give polymer B1-c 558. Further, operating adjustments 560 are made to give polymer B1-d 562. For a target polymer MFR range 564 of 35-55, a dual-catalyst system (HfP and Et-Ind) and initial reactor conditions are specified, as referenced by block 566. Operating adjustments 568 are made to give polymer B2 570. Operating adjustments 572 are made to give polymer B2-b 574. The adjustments 540, 548, 552, 556, 560, 568, and 572 are indicated in Table 1b above. Again, the reactor temperature and trim catalyst ratio may be primary variables or "knobs" for MFR. The comonomer/ethylene ratio, e.g., C6/C2 or C4/C2, may be a primary variable or "knob" for polymer density. The H2/C2 ratio may be a primary variable or "knob" for polymer MI.

Figure 6:
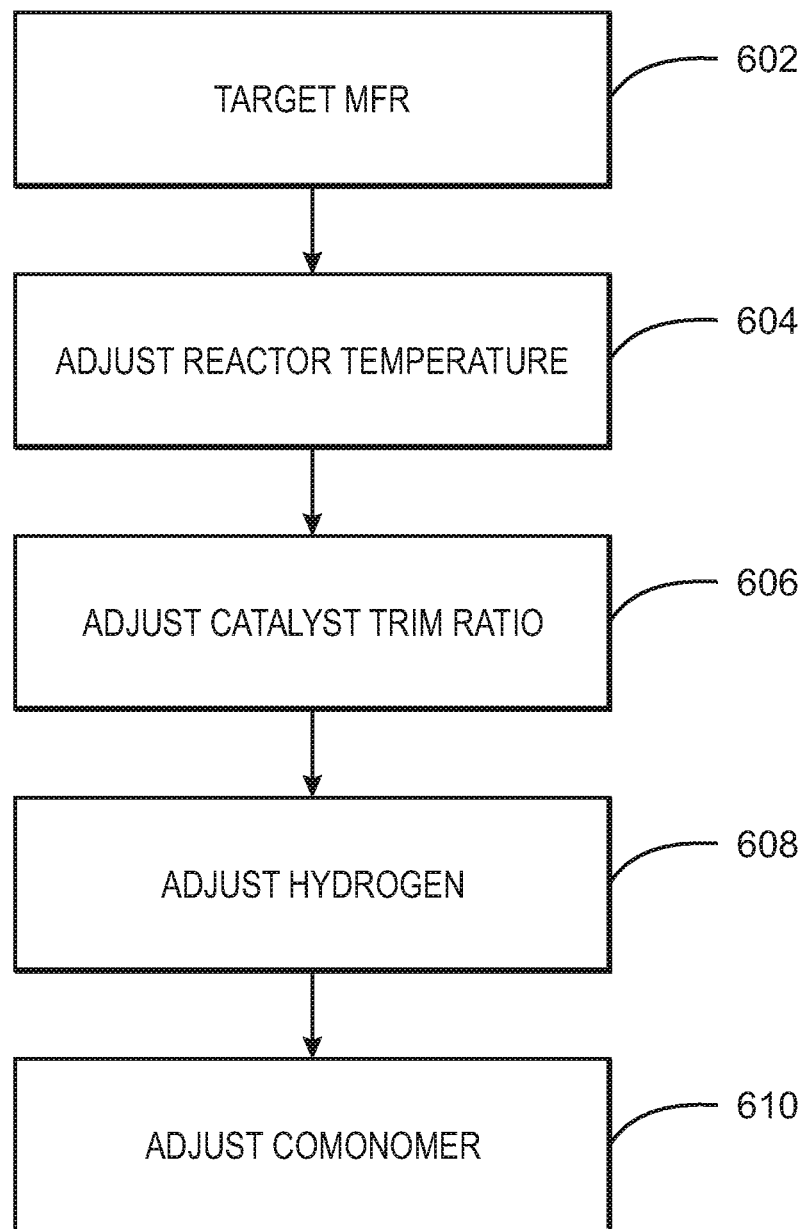
FIG. 6 is an exemplary method 600 for producing polyethylene including polyethylene having BOCD.

FIG. 6 is an exemplary method 600 for producing polyethylene including polyethylene having BOCD. The method 600 may involve developing recipe targets for the production of polyethylene, evaluating the production of potential BOCD polymer, and/or the actual real-time control in the production of polyethylene, and so forth. At block 602, a target MFR of the polyethylene polymer is desired or specified. In certain embodiments, the method 600 may involve a range of polymer MFR over the same MI and same density. The polymerization reactor temperature and the catalyst trim ratio (if a second catalyst is employed) are specified or adjusted to give the desired polymer MFR, as indicated by blocks 604 and 606. At block 608, the amount of hydrogen is specified or adjusted to maintain polymer MI. The adjustment may be to the hydrogen/ethylene (H2/C2) ratio in the polymerization mixture in the reactor. At block 610, the amount of comonomer is specified or adjusted to maintain polymer density. The adjustment may be to the comonomer/ethylene (e.g., C6/C2 or C4/C2) ratio in a feed stream to the reactor and/or in the polymerization mixture in the reactor.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A method of producing polyethylene, comprising:
    polymerizing ethylene in presence of a catalyst system in a reactor to form polyethylene, wherein the catalyst system comprises a first catalyst and a second catalyst, wherein the first catalyst is fed in a slurry to the reactor and the second catalyst is fed in a solution that is mixed with the slurry, wherein a molar ratio of the first catalyst to the second catalyst after the slurry and solution have been mixed to form the catalyst composition is from 500:1 to 1:500; and
    during polymerizing the ethylene, adjusting reactor conditions including at least one of hydrogen concentration, and comonomer concentration and an amount of the second catalyst fed to the reactor to control melt index (MI) and density of the polyethylene based on a target melt flow ratio (MFR) in a range of from 20 to 60, wherein the MFR is a ratio of flow index $(I_{21})$/MI, and wherein the density is in a range of from 0.912 to 0.940 g/cm$^3$ as measured in accordance with ASTM D-792, the polyethylene having:
    a value for Mw1/Mw2 of at least about 2.0, wherein Mw1/Mw2 is a ratio of a weight average molecular weight (Mw1) for a first half of a temperature rising elution (TREF) curve to a weight average molecular weight (Mw2) for a second half of the TREF curve; and
    a value for Tw1−Tw2 of less than about −15° C., wherein Tw1−Tw2 is a difference of a weight average elution temperature (Tw1) for the first half of the TREF curve to a weight average elution temperature (Tw2) for the second half of the TREF curve.

2. The method of claim 1, wherein adjusting reactor conditions comprises adjusting an operating temperature of the reactor.

3. The method of claim 1, wherein adjusting reactor conditions comprises adjusting a comonomer concentration in a polymerization mixture in the reactor.

4. The method of claim 1, wherein adjusting reactor conditions comprises adjusting hydrogen concentration in a polymerization mixture in the reactor.

5. The method of claim 1, wherein adjusting reactor conditions comprises adjusting a reactant concentration in a polymerization mixture in the reactor to meet a MI target of the polyethylene over a MFR range of the polyethylene.

6. The method of claim 1, wherein adjusting reactor conditions comprises adjusting a reactant concentration in a polymerization mixture in the reactor to meet a density target of the polyethylene over a MFR range of the polyethylene.

7. The method of claim 1, wherein the first catalyst comprises bis(n-propylcyclopentadienyl) Hafnium dimethyl.

8. The method of claim 1, wherein the second catalyst comprises di(1-ethylindenyl) zirconium dimethyl.

9. The method of claim 1, comprising impregnating the first catalyst and the second catalyst on a single support, wherein the catalyst system comprises a common-supported catalyst system.

10. The method of claim 1, wherein first catalyst promotes polymerization of the ethylene into a high molecular-weight portion of the polyethylene, and wherein the second catalyst promotes polymerization of the ethylene into a low molecular-weight portion of the polyethylene.

* * * * *

UNITED STATES PATENT AND TRADEMARK OFFICE
CERTIFICATE OF CORRECTION

| | |
|---|---|
| PATENT NO. | : 10,253,121 B2 |
| APPLICATION NO. | : 15/117343 |
| DATED | : April 9, 2019 |
| INVENTOR(S) | : Timothy M. Boller et al. |

It is certified that error appears in the above-identified patent and that said Letters Patent is hereby corrected as shown below:

In the Claims

Column 36, Lines 8-10 Claim 1 should recite, in part, "...wherein a molar ratio of the first catalyst to the second catalyst after the slurry and solution have been mixed to form the catalyst system is from 500:1 to 1:500..."

Signed and Sealed this
Fifth Day of September, 2023

Katherine Kelly Vidal
*Director of the United States Patent and Trademark Office*